United States Patent
Boehme et al.

(10) Patent No.: US 8,809,324 B2
(45) Date of Patent: Aug. 19, 2014

(54) SUBSTITUTED PHENYL-OXATHIAZINE DERIVATIVES, METHOD FOR PRODUCING THEM, DRUGS CONTAINING SAID COMPOUNDS AND THE USE THEREOF

(75) Inventors: Thomas Boehme, Frankfurt am Main (DE); Kurt Ritter, Frankfurt am Main (DE); Christian Engel, Frankfurt am Main (DE); Torsten Haack, Frankfurt am Main (DE); Stefan Guessregen, Frankfurt am Main (DE); Georg Tschank, Frankurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/003,395

(22) PCT Filed: Mar. 7, 2012

(86) PCT No.: PCT/EP2012/053933
§ 371 (c)(1),
(2), (4) Date: Sep. 5, 2013

(87) PCT Pub. No.: WO2012/120050
PCT Pub. Date: Sep. 13, 2012

(65) Prior Publication Data
US 2013/0345127 A1 Dec. 26, 2013

(30) Foreign Application Priority Data
Mar. 8, 2011 (EP) .................................... 11305238

(51) Int. Cl.
*A61K 31/51* (2006.01)
*C07D 291/06* (2006.01)
*C07D 419/10* (2006.01)
*A61K 45/06* (2006.01)
*A61K 31/54* (2006.01)

(52) U.S. Cl.
CPC ............ *C07D 291/06* (2013.01); *C07D 419/10* (2013.01); *A61K 45/06* (2013.01); *A61K 31/54* (2013.01)

USPC .......................... 514/222.5; 514/222.2; 544/2

(58) Field of Classification Search
None
See application file for complete search history.

(56) References Cited

FOREIGN PATENT DOCUMENTS

JP 60-214743 A 10/1985

OTHER PUBLICATIONS

Suzue, Seigo and Irikura, Tutomu; "Studies on hypoglycemic agents IV. Synthesis of 1, 4, 3-benzoxantiazine-4,4-dioxides." Chem. Pharm. Bull. (1968) 16(5) p. 806-813.*
Seigo Suzue et al., Studies on Hypoglycemic Agents. IV. 1) Synthesis of 1,4,3-Benzoxathiazine-4,4-dioxides, Chemical and Pharmaceutical Bulletin, (May 25, 1968), vol. 16, No. 5, pp. 806-813.
International Search Report dated Jun. 26, 2012 issued in PCT/EP2012/053933.

* cited by examiner

*Primary Examiner* — James H. Alstrum Acevedo
*Assistant Examiner* — Fred Reynolds
(74) *Attorney, Agent, or Firm* — Scully, Scott, Murphy & Presser, P.C.

(57) ABSTRACT

The invention relates to the compounds of formula (I) and to the physiologically acceptable salts thereof. Said compounds are suitable e.g. for the treatment of hyperglycemia.

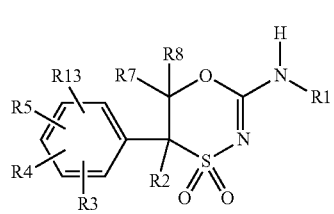

13 Claims, No Drawings

SUBSTITUTED PHENYL-OXATHIAZINE DERIVATIVES, METHOD FOR PRODUCING THEM, DRUGS CONTAINING SAID COMPOUNDS AND THE USE THEREOF

The invention relates to substituted phenyloxathiazine derivatives and to the physiologically compatible salts thereof.

It was an object of the invention to provide compounds which display a therapeutically utilizable action. More particularly, it was a further object to find novel compounds suitable for treatment of diabetes, hyperglycemia, insulin resistance, obesity or lipid metabolism disorders.

The invention therefore relates to compounds of the formula I

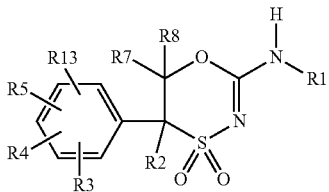

in which
R1 is

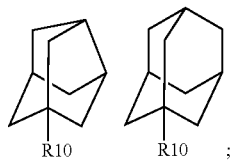

R2 is H, F, $(C_1-C_3)$-alkyl where the alkyl radical may be mono- to trisubstituted by fluorine;
R3, R4, R5, R13 are each independently
H, F, Cl, Br, I, OH, $CF_3$, $CHF_2$, $CH_2F$, $NO_2$, CN, $OCF_3$, $OCHF_2$, —$(C_1-C_6)$-alkylene-(R9), O—$(C_1-C_6)$-alkylene-(R9), tert-butyl, isopropylene-(R9), (C=O)—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-R9$)_2$, $(C_1-C_6)$-alkylene-$NH_2$, $(C_1-C_6)$-alkylene-$NH(C_1-C_6)$-alkylene-(R9), $(C_1-C_6)$-alkylene-$N((C_1-C_6)$-alkylene-R9$)_2$, —O—$(C_1-C_6)$-alkylene-$NH_2$, —O—$(C_1-C_6)$-alkylene-$NH(C_1-C_6)$-alkylene-(R9), —O—$(C_1-C_6)$-alkylene-$N((C_1-C_6)$-alkylene-R9$)_2$, —NH—$(C_1-C_6)$-alkylene-$NH_2$, —NH—$(C_1-C_6)$-alkylene-$NH(C_1-C_6)$-alkylene-(R9), —NH—$(C_1-C_6)$-alkylene-$N((C_1-C_6)$-alkylene-R9$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
$(C_6-C_{10})$-aryl, —$(C_1-C_6)$-alkylene-$(C_6-C_{10})$-aryl,
where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
$(C_6-C_{10})$-aryl, $(C_3-C_7)$-cycloalkyl, 4- to 12-membered heterocycle;
where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
4- to 12-membered heterocycle, —$(C_1-C_6)$-alkylene-4- to –12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_a)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$—$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$, $(C_6-C_{10})$-aryl, $(C_3-C_7)$-cycloalkyl, 4- to 12-membered heterocycle;
where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
R7, R8 are each independently H, $(C_1-C_3)$-alkyl, where the alkyl radical may be mono- to trisubstituted by fluorine, or R7 and R8 together with the carbon atom to which they are bonded form a 3-7-membered carbocycle or heterocycle;
R9 is H, OH, $OCH_3$, $OCF_3$, $CHF_2$, $CF_3$;
R10 is H, $CONH_2$;
and pharmaceutically compatible salts thereof.

A further embodiment relates to compounds of the formula I in which one or more radicals are defined as follows:
R1 is

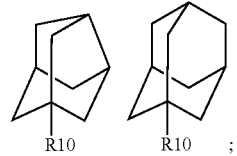

R2 is H, $(C_1-C_3)$-alkyl;
R3, R4, R5, R13 are each independently
H, F, Cl, Br, I, OH, $CF_3$, $CHF_2$, $CH_2F$, $NO_2$, CN, $OCF_3$, $OCHF_2$, —$(C_1-C_6)$-alkylene-(R9), O—$(C_1-C_6)$-alkylene-(R9), tert-butyl, isopropylene-(R9), (C=O)—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-R9$)_2$, $(C_1-C_6)$-alkylene-$NH_2$, $(C_1-C_6)$-alkylene-$NH(C_1-C_6)$-alkylene-(R9), $(C_1-C_6)$-alkylene-$N((C_1-C_6)$-alkylene-R9$)_2$, —O—$(C_1-C_6)$-alkylene-$NH_2$, —O—$(C_1-C_6)$-alkylene-$NH(C_1-C_6)$-alkylene-(R9), —O—$(C_1-C_6)$-alkylene-$N((C_1-C_6)$-alkylene-R9$)_2$, —NH—$(C_1-C_6)$-alkylene-$NH_2$, —NH—$(C_1-C_6)$-alkylene-$NH(C_1-C_6)$-alkylene-(R9), —NH—$(C_1-C_6)$-alkylene-$N((C_1-C_6)$-alkylene-R9$)_2$, $SO_2$—$CH_3$, $SO_2$—$NH_2$, $SO_2$—$NH(C_1$-

$C_6$)-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

($C_6$-$C_{10}$)-aryl, —($C_1$-$C_6$)-alkylene-($C_6$-$C_{10}$)-aryl,
  where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6)$-alkyl, $CONH_2$, $CONH(C_1$-$C_6)$-alkyl, $CON((C_1$-$C_6)$-alkyl$)_2$, $SF_5$, ($C_6$-$C_{10}$)—aryl, ($C_3$-$C_7$)-cycloalkyl, 4- to 12-membered heterocycle;
    where the ($C_6$-$C_{10}$)-aryl radical, ($C_3$-$C_7$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6)$-alkyl, $CONH_2$, $CONH(C_1$-$C_6)$-alkyl, $CON((C_1$-$C_6)$-alkyl$)_2$, $SF_5$;

4- to 12-membered heterocycle, —($C_1$-$C_6$)-alkylene-4- to –12-membered heterocycle,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl$)_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl$)_2$, COOH, COO—($C_1$-$C_6)$-alkylene-(R9), $CONH_2$, $CONH(C_1$-$C_6)$-alkylene-(R9), $CON((C_1$-$C_6)$-alkyl$)_2$, $SF_5$, ($C_6$-$C_{10}$)-aryl, ($C_3$-$C_7$)-cycloalkyl, 4- to 12-membered heterocycle;
    where the ($C_6$-$C_{10}$)-aryl radical, ($C_3$-$C_7$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6)$-alkyl, $CONH_2$, $CONH(C_1$-$C_6)$-alkyl, $CON((C_1$-$C_6)$-alkyl$)_2$, $SF_5$;

R7, R8 are each independently H, ($C_1$-$C_3$)-alkyl;
R9 is H, OH, $OCH_3$, $OCF_3$, $CHF_2$, $CF_3$;
R10 is H, $CONH_2$;
and pharmaceutically compatible salts thereof.

A further embodiment relates to compounds of the formula I in which one or more radicals have the following meanings:
R1 is

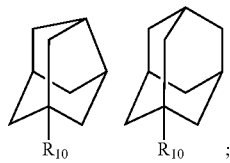

R2 is H;
R3, R4, R5, R13 are each independently
  H, F, Cl, Br, I, OH, $CF_3$, $NO_2$, CN, $OCF_3$, $OCHF_2$, —($C_1$-$C_6$)-alkylene, —O—($C_1$-$C_6$)-alkylene;
($C_6$-$C_{10}$)-aryl,
  where the aryl radical may be mono- to trisubstituted by F, Cl, Br, I, OH, $CF_3$, $CHF_2$, $CH_2F$, $NO_2$, CN, $OCF_3$, ($C_1$-$C_6$)-alkyl, $NH_2$, $NH(C_1$-$C_6)$-alkyl, $N((C_1$-$C_6)$-alkyl$)_2$, $SO_2$—$NH_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6)$-alkyl, $CONH_2$, $CONH(C_1$-$C_6)$-alkyl, $CON((C_1$-$C_6)$-alkyl$)_2$, $SF_5$;
4- to 12-membered heterocycle,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl$)_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl$)_2$, COOH, COO—($C_1$-$C_6)$-alkylene-(R9), $CONH_2$, $CONH(C_1$-$C_6)$-alkylene-(R9), $CON((C_1$-$C_6)$-alkyl$)_2$, $SF_5$;

R7, R8 is H, ($C_1$-$C_3$)-alkyl;
R9 is H, OH, $OCH_3$, $OCF_3$, $CHF_2$, $CF_3$;
R10 is H, $CONH_2$;
and pharmaceutically compatible salts thereof.

A further embodiment relates to compounds of the formula I in which one or more radicals have the following meanings:
R1 is

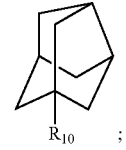

R2 is H;
R3, R4, R5 are each independently
  H, F, Cl, Br, I, OH, $CF_3$, $NO_2$, CN, $OCF_3$, $OCHF_2$, —($C_1$-$C_6$)-alkylene, —O—($C_1$-$C_6$)-alkylene;
phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6)$-alkyl, $CONH_2$, $CONH(C_1$-$C_6)$-alkyl, $CON((C_1$-$C_6)$-alkyl$)_2$, $SF_5$;
piperidinyl,
  where the piperidinyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl$)_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl$)_2$, COON, COO—($C_1$-$C_6)$-alkylene-(R9), $CONH_2$, $CONH(C_1$-$C_6)$-alkylene-(R9), $CON((C_1$-$C_6)$-alkyl$)_2$, $SF_5$;

R13 is F, Cl, Br, I, OH, $CF_3$, $NO_2$, CN, $OCF_3$, $OCHF_2$, —($C_1$-$C_6$)-alkylene, —O—($C_1$-$C_6$)-alkylene;
phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—N ((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

piperidinyl,
where the piperidinyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—(C$_1$-C$_6$)-alkylene-(R9), SO$_2$—C$_2$H$_2$F$_3$, SO$_2$—CH$_3$, SO$_2$—NH$_2$, SO$_2$—NH(C$_1$-C$_6$)-alkylene-(R9), SO$_2$—N((C$_1$-C$_6$)-alkyl)$_2$, COOH, COO—(C$_1$-C$_6$)-alkylene-(R9), CONH$_2$, CONH(C$_1$-C$_6$)-alkylene-(R9), CON((C$_1$-C$_6$)-alkyl)$_2$, SF$_5$;

R7, R8 is H, (C$_1$-C$_3$)-alkyl;
R9 is H, OH, OCH$_3$, OCF$_3$, CHF$_2$, CF$_3$;
R10 is H, CONH$_2$;
and pharmaceutically compatible salts thereof.

A further embodiment relates to compounds of the formula I in which the R1 radical is bonded as shown in formula Ia and Ib.

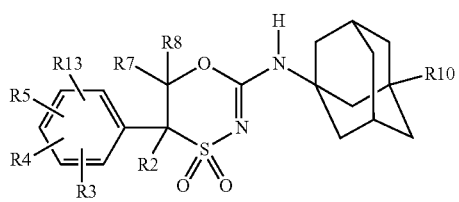

Ia

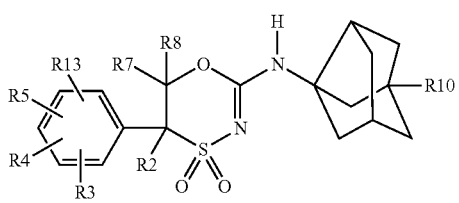

Ib

If radicals or substituents occur more than once in the compounds of the formula I, they may each independently be defined as specified and be the same or different.

The invention relates to compounds of the formula I in the form of their tautomers, racemates, racemic mixtures, stereoisomer mixtures, pure stereoisomers, diastereoisomer mixtures and pure diastereoisomers. The mixtures are separated, for example, by a chromatographic route.

Because of their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, are likewise within the scope of the invention as useful intermediates for the preparation or purification of pharmaceutically acceptable salts and/or for use in nontherapeutic, for example in vitro, applications.

The inventive compounds may also exist in various polymorphic forms, for example as amorphous and crystalline polymorphic forms. All polymorphic forms of the inventive compounds are within the scope of the invention and are a further aspect of the invention.

All references to "compound(s) of formula I" hereinafter refer to compound(s) of the formula I as described above, and the salts and solvates thereof as described herein.

An alkyl radical is understood to mean a straight-chain or branched hydrocarbon chain having one to eight carbons, for example methyl, ethyl, isopropyl, tert-butyl, hexyl, heptyl, octyl. The alkyl radicals may be mono- or polysubstituted as described above.

An alkylene radical is understood to mean a straight-chain or branched hydrocarbon chain having two free valences, for example methylene, ethylene, isopropylene, tert-butylene.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above. Heterocycle and heterocyclic radical are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydro-benzothiazol-2-yl, 4,5,6,7-tetrahydrobenzoimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The compound(s) of the formula I can also be administered in combination with further active ingredients.

The amount of a compound of the formula I required to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other ingredients of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The inventive pharmaceutical compositions can be produced by one of the known pharmaceutical methods, which essentially involve mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination products are:

All antidiabetics mentioned in the Rote Liste 2006, chapter 12; all weight-reducing agents/appetite suppressants mentioned in the Rote Liste 2006, chapter 1; all lipid-lowering agents mentioned in the Rote Liste 2006, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives, for example Lantus® (see www.lantus.com) or HMR 1964 or Levemir® (insulin detemir), or those as described in WO2005005477 (Novo Nordisk), fast-acting insulins (see U.S. Pat. No. 6,221,633), inhalable insulins, for example Exubera®, or oral insulins, for example IN-105 (Nobex) or Oral-lyn™ (Generex Biotechnology), GLP-1 derivatives, for example exenatide, liraglutide or those which have been disclosed in WO 98/08871, WO2005027978, WO2006037811, WO2006037810 to Novo Nordisk A/S, in WO 01/04156 to Zealand or in WO 00/34331 to Beaufour-Ipsen, pramlintide acetate (Symlin; Amylin Pharmaceuticals), and orally active hypoglycemic ingredients.

The orally active hypoglycemic ingredients preferably include sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists, potassium channel openers, for example those which have been disclosed in WO 97/26265 and WO 99/03861 to Novo Nordisk A/S, or those described in WO2006045799 (Solvay),
inhibitors of dipeptidyl peptidase-IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase-1B (PTP1B),
modulators of sodium-dependent glucose transporter 1 or 2 (SGLT1, SGLT2),
compounds which modify the lipid metabolism, such as active antihyperlipidemic ingredients and active antilipidemic ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG).

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with fenofibrate.

In a further embodiment of the invention, the compound of the formula I is administered in combination with a solid combination of fenofibrate with rosuvastatin.

In one embodiment of the invention, the compound of the formula I is administered in combination with ISIS-301012, an antisense oligonucleotide which is capable of regulating the apolipoprotein B gene.

In one embodiment of the invention, the compound of the formula I is administered in combination with a PPAR gamma agonist, for example rosiglitazone, pioglitazone, JTT-501, GI 262570, R-483, CS-011 (rivoglitazone).

In one embodiment of the invention, the compound of the formula I is administered in combination with Competact™, a solid combination of pioglitazone hydrochloride with metformin hydrochloride.

In one embodiment of the invention, the compound of the formula I is administered in combination with Duetact™, a solid combination of pioglitazone hydrochloride with glimepiride.

In one embodiment of the invention, the compound of the formula I is administered in combination with Avandamet®, a solid combination of rosiglitazone maleate with metformin hydrochloride.

In one embodiment of the invention, the compound of the formula I is administered in combination with PPAR alpha agonists, for example GW9578, GW-590735, K-111, LY-674, KRP-101, DRF-10945.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist, for example GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK), for example A-769662 or those compounds as described in US20050038068.

In one embodiment of the invention, the compound of the formula I is administered in combination with a fibrate, for example fenofibrate, clofibrate, bezafibrate.

In one embodiment of the invention, the compound of the formula I is administered in combination with an MTP inhibitor, for example implitapide, BMS-201038, R-103757 or those as described in WO2005085226, WO2005121091, WO2006010423.

In one embodiment of the invention, the compound of the formula I is administered in combination with a CETP inhibitor, for example torcetrapib or JTT-705, or those as described in WO2006002342, WO2006010422, WO2006012093.

In one embodiment of the invention, the compound of the formula I is administered in combination with bile acid reabsorption inhibitor (see, for example, U.S. Pat. Nos. 6,245,744, 6,221,897 or WO00/61568), for example HMR 1741, or those as described in DE 10 2005 033099.1 and DE 10 2005 033100.9.

In one embodiment of the invention, the compound of the formula I is administered in combination with a polymeric bile acid adsorber, for example cholestyramine, colesevelam.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor, for example avasimibe or SMP-797.

In one embodiment of the invention, the compound of the formula I is administered in combination with an antioxidant, for example OPC-14117, probucol, tocopherol, ascorbic acid, β-carotene or selenium.

In one embodiment of the invention, the compound of the formula I is administered in combination with a vitamin, for example vitamin B6 or vitamin B12.

In one embodiment of the invention, the compound of the formula I is administered in combination with a lipoprotein lipase modulator, for example ibrolipim (NO-1886).

In one embodiment of the invention, the compound of the formula I is administered in combination with an ATP citrate lyase inhibitor, for example SB-204990.

In one embodiment of the invention, the compound of the formula I is administered in combination with a squalene synthetase inhibitor, for example BMS-188494, or as described in WO2005077907.

In one embodiment of the invention, the compound of the formula I is administered in combination with a lipoprotein (a) antagonist, for example gemcabene (CI-1027).

In one embodiment of the invention, the compound of the formula I is administered in combination with an agonist of GPR109A (HM74A receptor agonist), for example nicotinic acid or "extended release niacin" in conjunction with MK-0524A, or those compounds as described in WO2006045565, WO2006045564, WO2006069242.

In another embodiment of the invention, the compound of the formula I is administered in combination with an agonist of GPR116, as described, for example, in WO2006067531, WO2006067532.

In one embodiment of the invention, the compound of the formula I is administered in combination with a lipase inhibitor, for example orlistat or cetilistat (ATL-962).

In one embodiment of the invention, the compound of the formula I is administered in combination with insulin.

In one embodiment, the compound of the formula I is administered in combination with a sulfonylurea, for example tolbutamide, glibenclamide, glipizide or glimepiride.

In one embodiment, the compound of the formula I is administered in combination with a substance which enhances insulin secretion, for example KCP-265 (WO2003097064).

In one embodiment, the compound of the formula I is administered in combination with agonists of the glucose-dependent insulinotropic receptor (GDIR), for example APD-668.

In one embodiment, the compound of the formula I is administered in combination with a biguanide, for example metformin.

In yet another embodiment, the compound of the formula I is administered in combination with a meglitinide, for example repaglinide or nateglinide.

In one embodiment, the compound of the formula I is administered in combination with a thiazolidinedione, for example troglitazone, ciglitazone, pioglitazone, rosiglitazone or the compounds disclosed in WO 97/41097 to Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor, for example miglitol or acarbose.

In one embodiment, the compound of the formula I is administered in combination with an active ingredient which acts on the ATP-dependent potassium channel of the beta cells, for example tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504 or as described in WO2004100875, WO2005065680.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923.

In one embodiment, the compound of the formula I is administered in combination with an inhibitor of gluconeogenesis, for example FR-225654.

In one embodiment, the compound of the formula I is administered in combination with inhibitors of fructose 1,6-bisphosphatase (FBPase), for example CS-917 (MB-06322) or MB-07803, or those as described in WO2006023515.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidylpeptidase-W (DPP-TV), for example vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964X, KRP-104, DP-893 or as described in WO2003074500, WO2003106456, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a solid combination of sitagliptin phosphate with metformin hydrochloride.

In one embodiment, the compound of the formula I is administered in combination with inhibitors of 11-beta-hydroxysteroid dehydrogenase 1 (11β-HSD1), for example BVT-2733, JNJ-25918646, INCB-13739, or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as described, for example, in WO200119830-31, WO200117516, WO2004506446, WO2005012295, WO2005116003, PCT/EP2005/005311, PCT/EP2005/005321, PCT/EP2005/007151, PCT/EP2005/01294 or DE 10 2004 060542.4.

In one embodiment, the compound of the formula I is administered in combination with modulators of sodium-dependent glucose transporter 1 or 2 (SGLT1, SGLT2), for example KGA-2727, T-1095, SGL-0010, AVE 2268 and SAR 7226, or as described, for example, in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with GPR40 modulators.

In one embodiment, the compound of the formula I is administered in combination with GPR119b modulators, as described, for example, in WO2004041274.

In one embodiment, the compound of the formula I is administered in combination with GPR119 modulators, as described, for example, in WO2005061489 (PSN-632408).

In one embodiment, the compound of the formula I is administered in combination with inhibitors of hormone-sensitive lipase (HSL), as described, for example, in WO2005073199.

In one embodiment, the compound of the formula I is administered in combination with inhibitors of acetyl-CoA carboxylase (ACC), for example those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of glycogen synthase kinase-3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), for example ruboxistaurin.

In one embodiment, the compound of the formula I is administered in combination with an endothelin A receptor antagonist, for example avosentan (SPP-301).

In one embodiment, the compound of the formula I is administered in combination with inhibitors of "I-kappaB kinase" (IKK inhibitors), as described, for example, in WO2001000610, WO2001030774, WO2004022553, WO2005097129.

In one embodiment, the compound of the formula I is administered in combination with modulators of the glucocorticoid receptor, as described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A); NPY-5 receptor antagonists such as L-152804, S-2367 or as described, for example, in WO2006001318;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424;

CB1R (cannabinoid receptor 1) antagonists (for example rimonabant, SR147778, SLV-319, AVE-1625, MK-0364 or salts thereof, or those as described in, for example, EP 0656354, WO 00/15609, WO2001/64632, WO2001/64633, WO2001/64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443);

MC4 agonists (for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2005037797, WO2005042516, WO2005040109, WO2005030797, US20040224901, WO200501921, WO200509184, WO2005000339, EP1460069, WO2005047253, WO2005047251, EP1538159, WO2004072076, WO2004072077, WO2006021655-57;

orexin receptor antagonists (for example 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224);

histamine H3 receptor agonists (for example 3-cyclohexyl-1-(4,4-dimethyl-1,4,6,7-tetrahydroimidazo[4,5-c]pyridin-5-yl)-propan-1-one oxalic acid salt (WO 00/63208), or those as described in WO200064884, WO2005082893);

CRF antagonists (for example [2-Methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]-ethanol hydrochloride (WO 01/83451) or solabegron (GW-427353) or N-5984 (KRP-204), or those as described in JP2006111553;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430, or those compounds as described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034;

serotonin reuptake inhibitors (for example dexfenfluramine);

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

5-HT2C receptor agonists (for example lorcaserine hydrochloride (APD-356) or BVT-933, or those as described in WO200077010, WO20077001-02, WO2005019180, WO2003064423, WO200242304, WO2005082859);

5-HT6 receptor antagonists, as described, for example in WO2005058858;

bombesin receptor agonists (BRS-3 agonists);

galanin receptor antagonists;

growth hormone (e.g. human growth hormone or AOD-9604);

growth hormone-releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

dopamine agonists (DA agonists, for example bromocriptine, Doprexin);

lipase/amylase inhibitors (e.g. WO 00/40569);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS), for example C75, or those as described in WO2004005277;

oxyntomodulin;

oleoyl-estrone or thyroid hormone receptor agonists, for example: KB-2115, or those as described in WO20058279, WO200172692, WO200194293, WO2003084915, WO2004018421, WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1, a member of the human sirtuin enzyme family.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermin.

In one embodiment, the further active ingredient is a diphenylazetidinone derivative, as described, for example, in U.S. Pat. Nos. 6,992,067 or 7,205,290.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

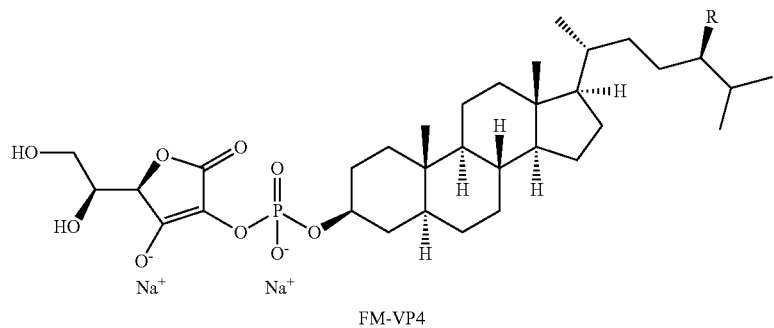
FM-VP4
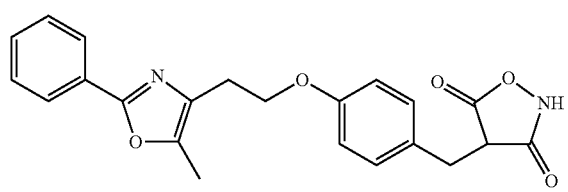
JTT-501
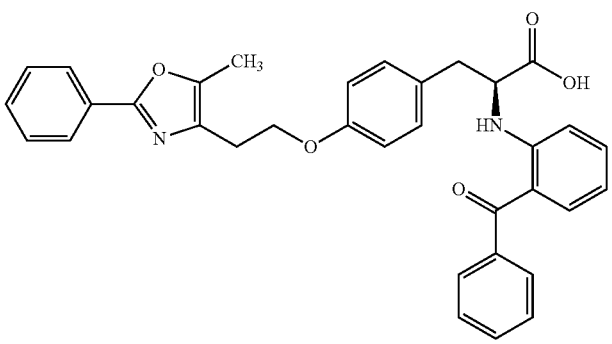
GI 262570
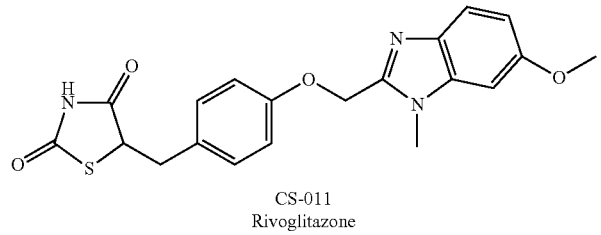
CS-011
Rivoglitazone
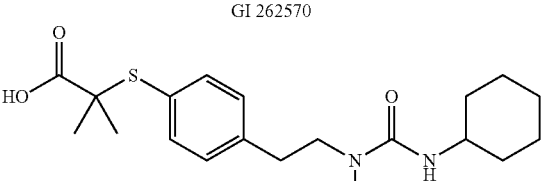
GW-9578
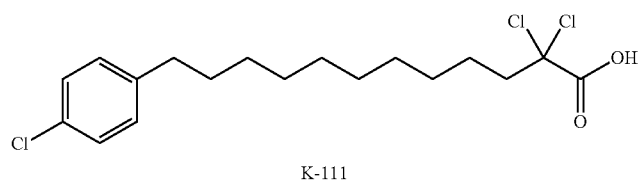
K-111
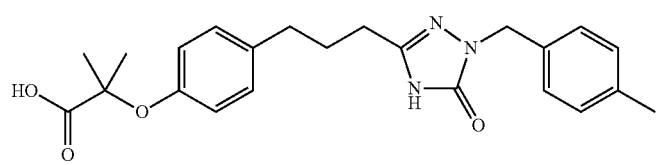
LY-518674
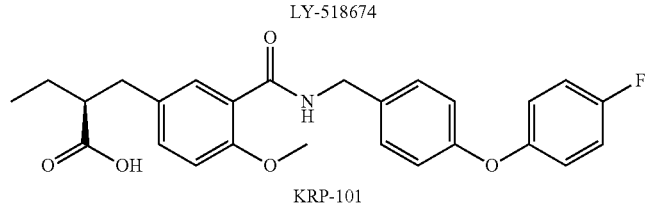
KRP-101

-continued
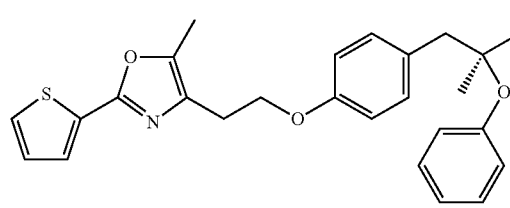
LY-510929
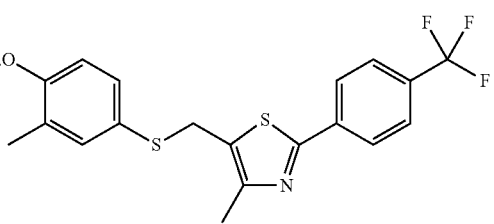
GW-501516
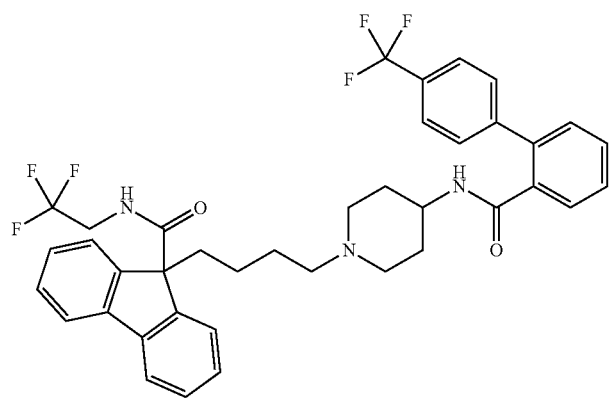
BMS-201038
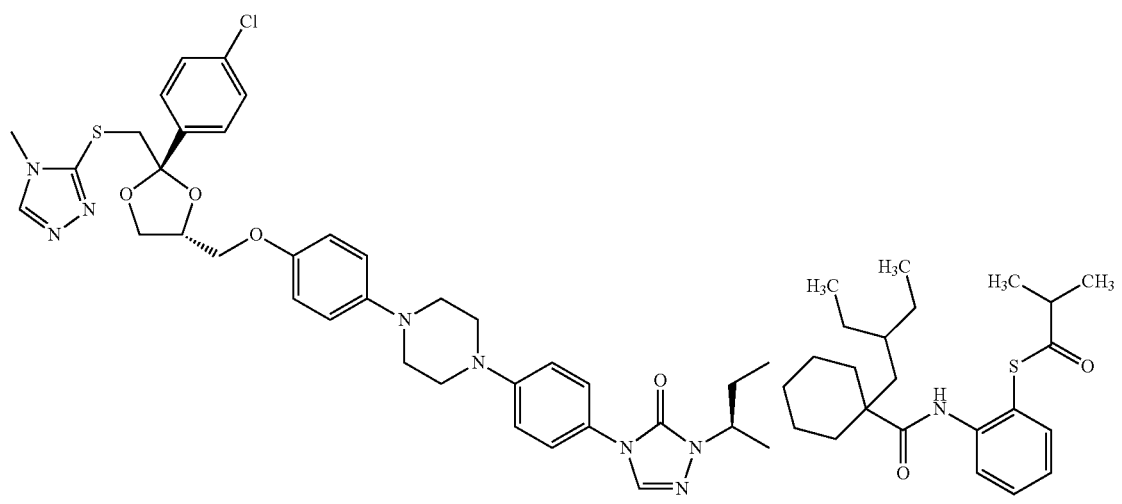
R-103757                    JTT-705
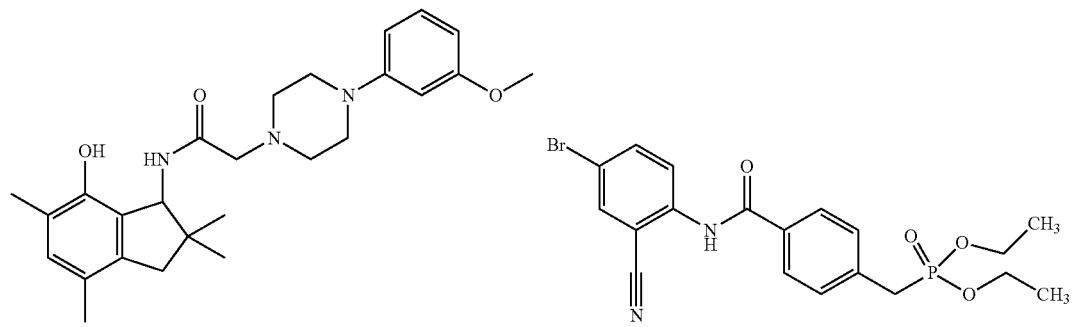
OPC-14117                   NO-1886

-continued
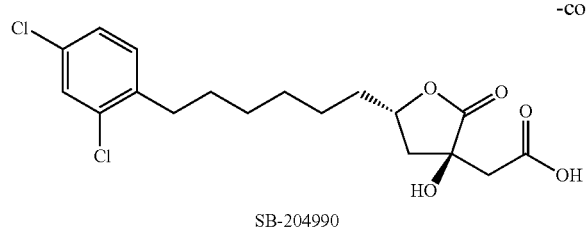
SB-204990
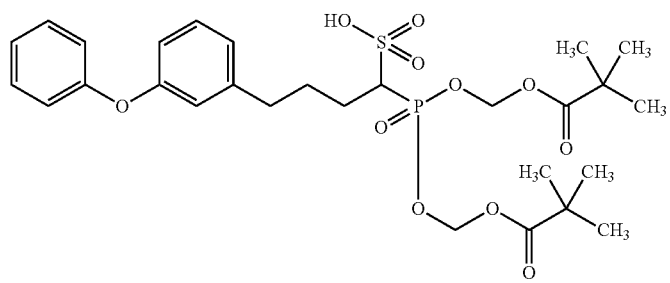
BMS-188494
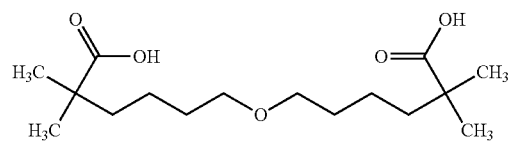
CI-1027
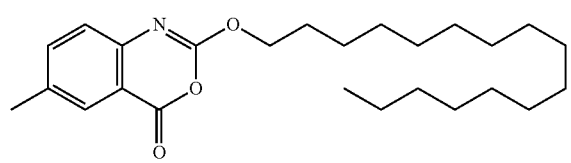
ATL-962
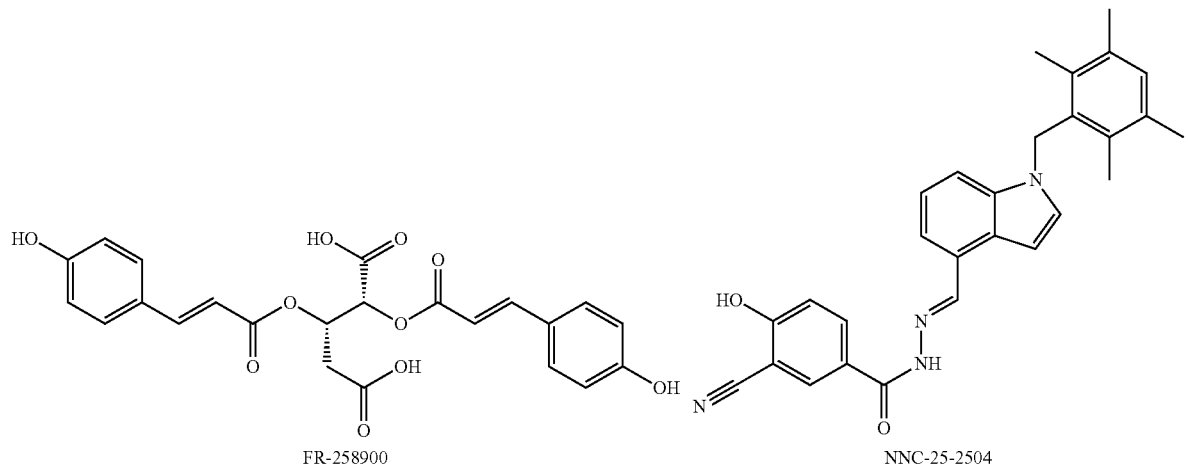
FR-258900
NNC-25-2504
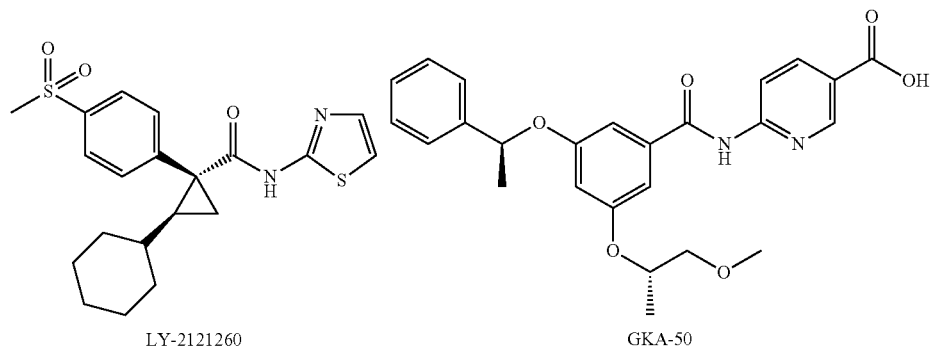
LY-2121260
GKA-50

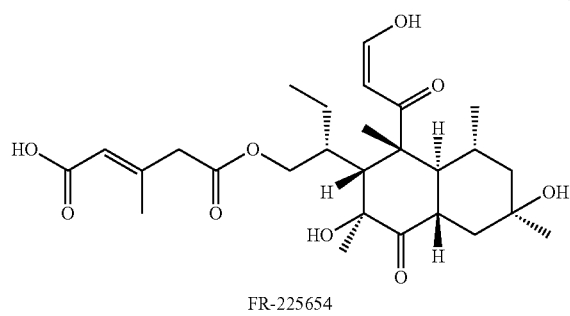
FR-225654
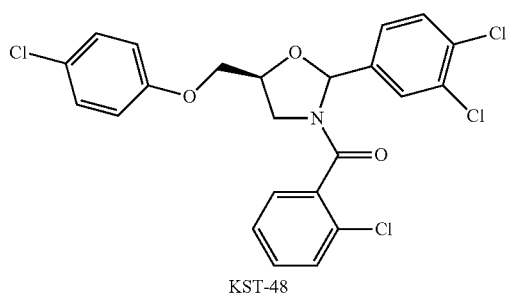
KST-48
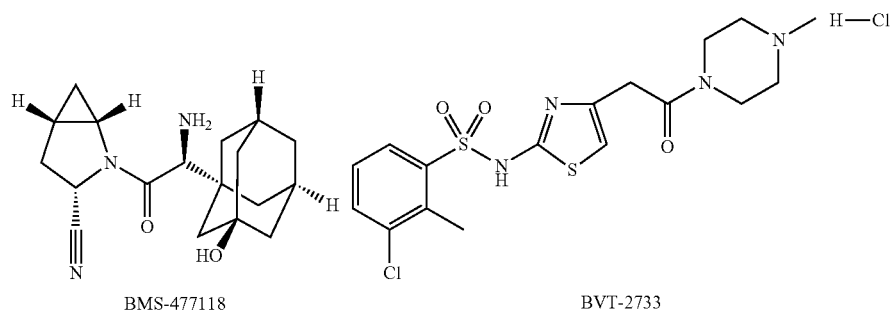
BMS-477118    BVT-2733
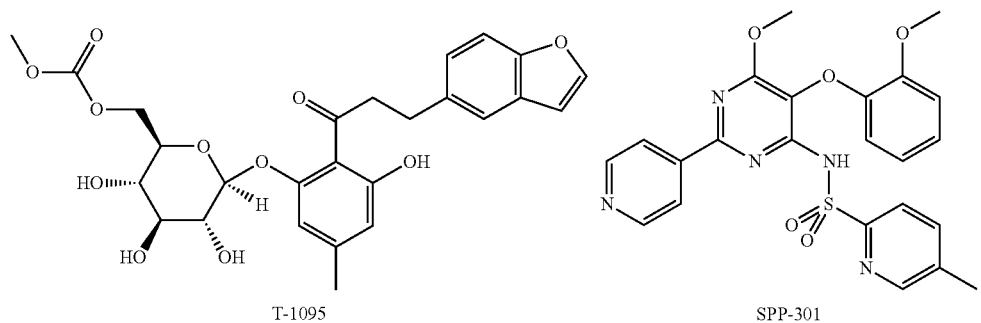
T-1095    SPP-301
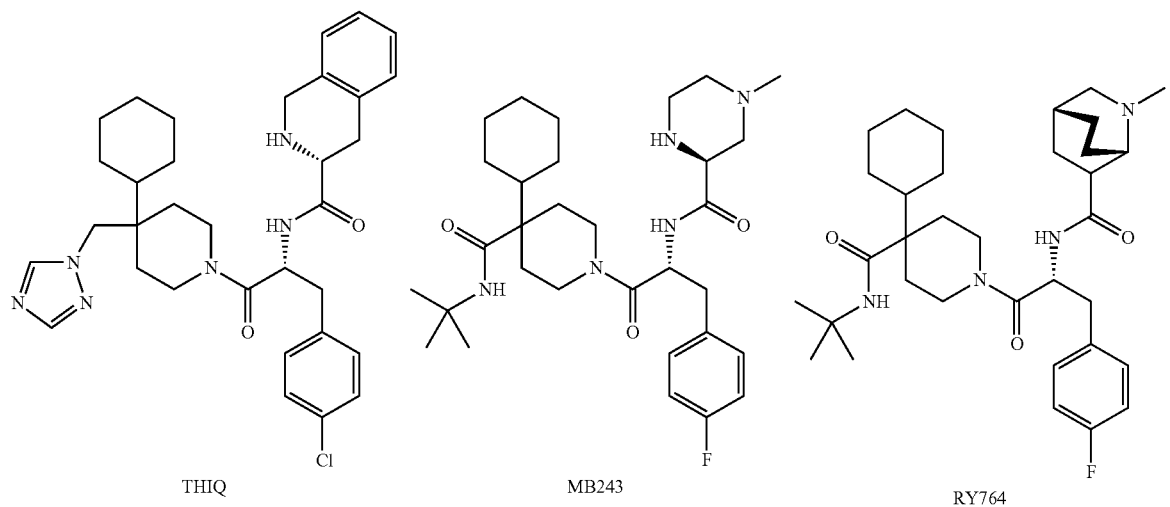
THIQ    MB243    RY764

-continued
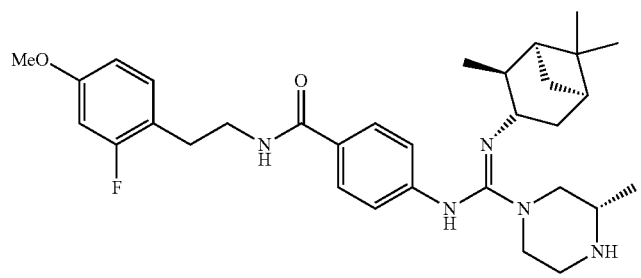
CHIR-785
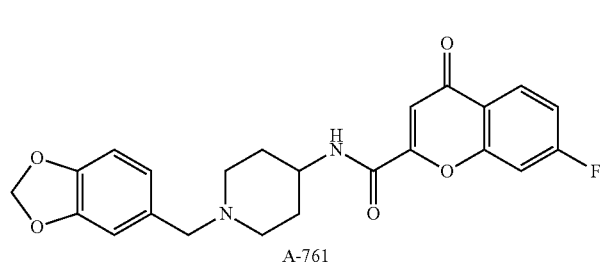
A-761
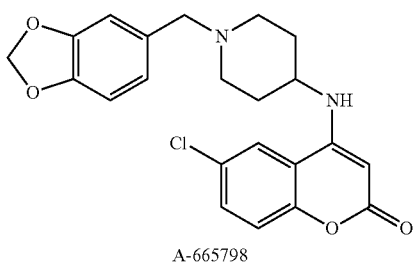
A-665798
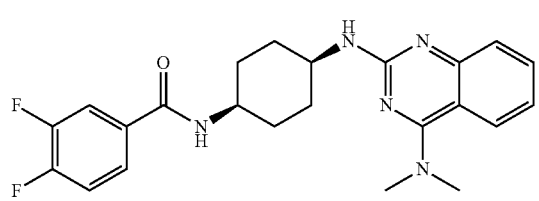
ATC-0175
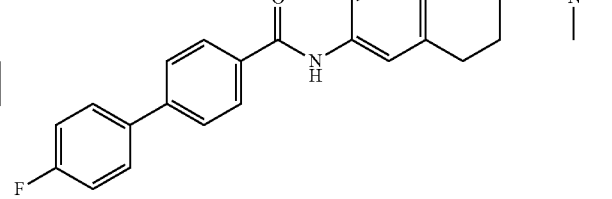
T-226296
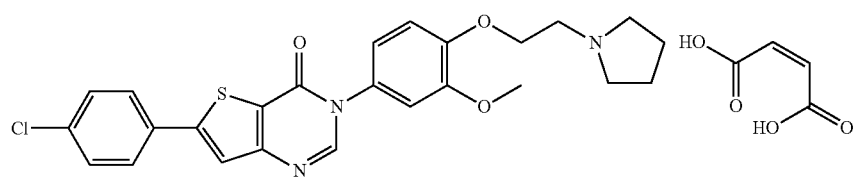
GW-803430
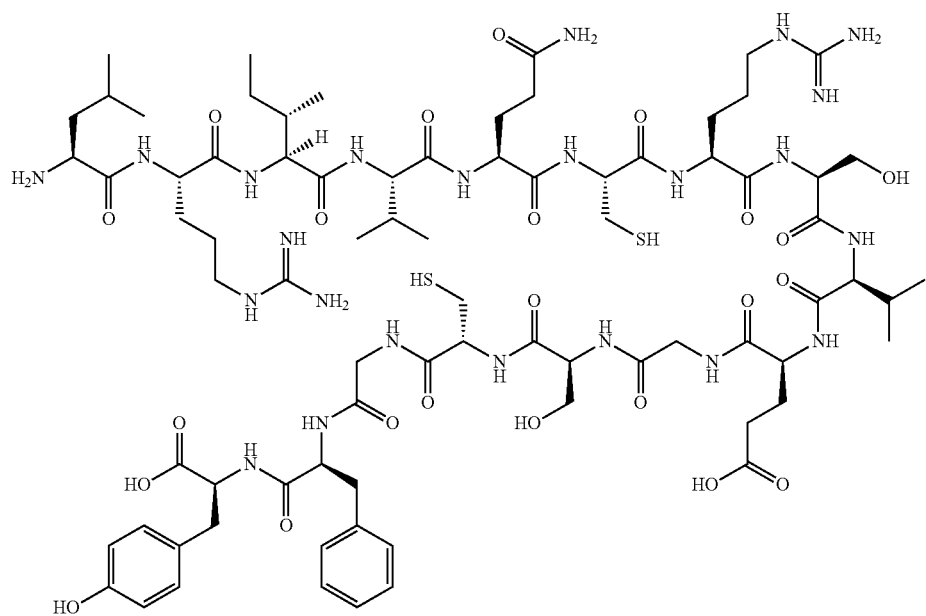
AOD-9604

-continued
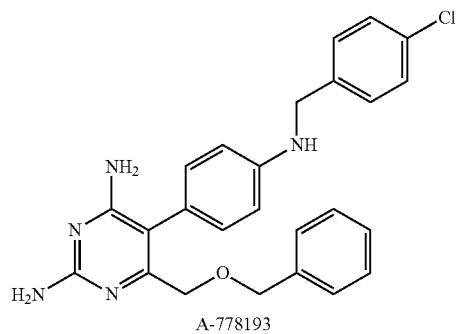
A-778193
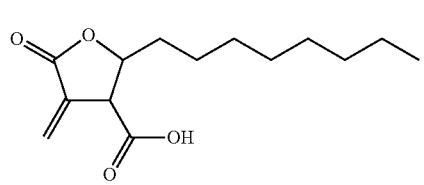
C75
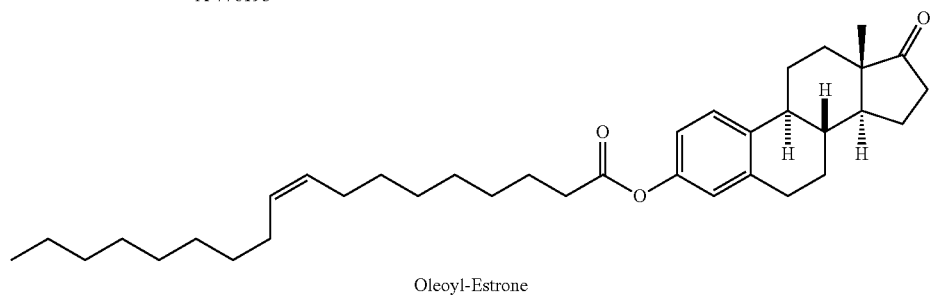
Oleoyl-Estrone
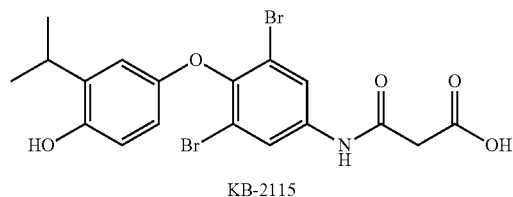
KB-2115
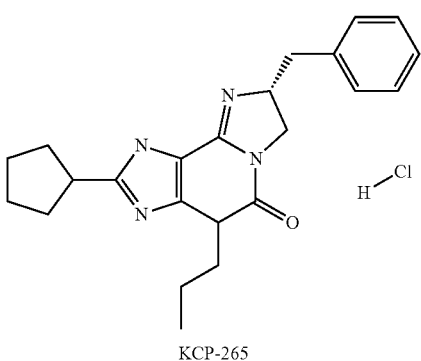
KCP-265
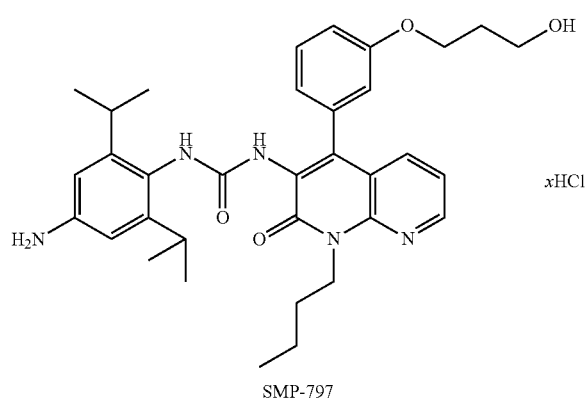
SMP-797
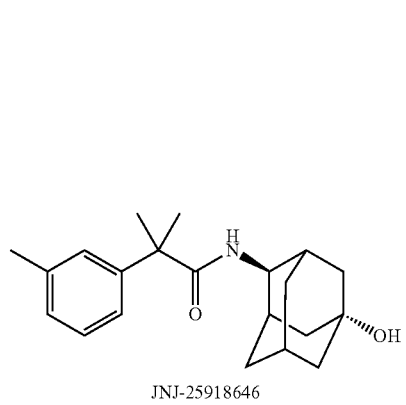
JNJ-25918646
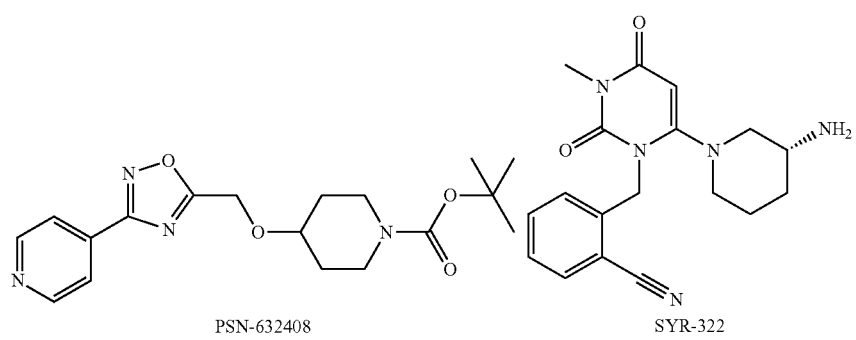
PSN-632408          SYR-322

-continued
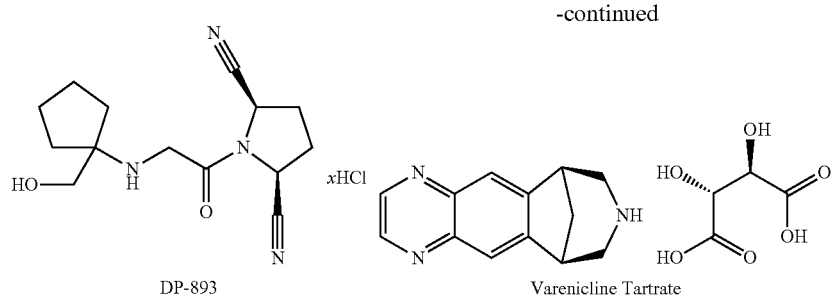
DP-893        Varenicline Tartrate
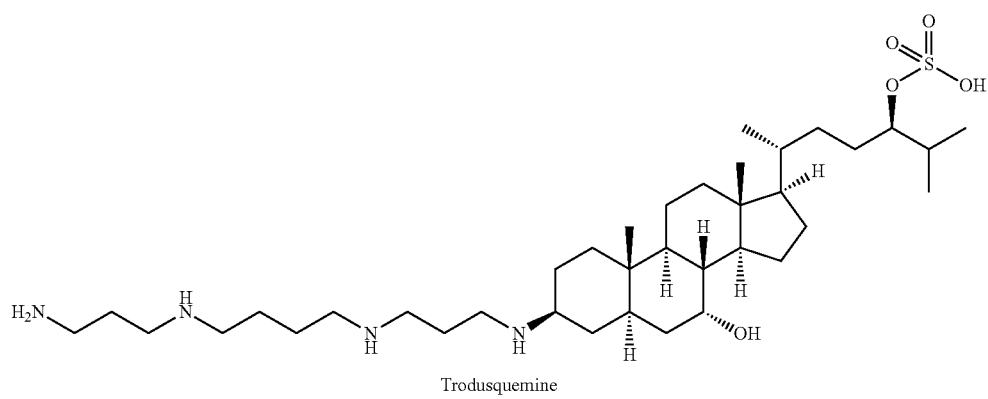
Trodusquemine
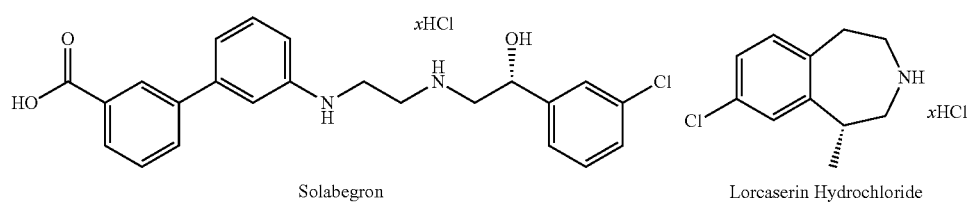
Solabegron        Lorcaserin Hydrochloride
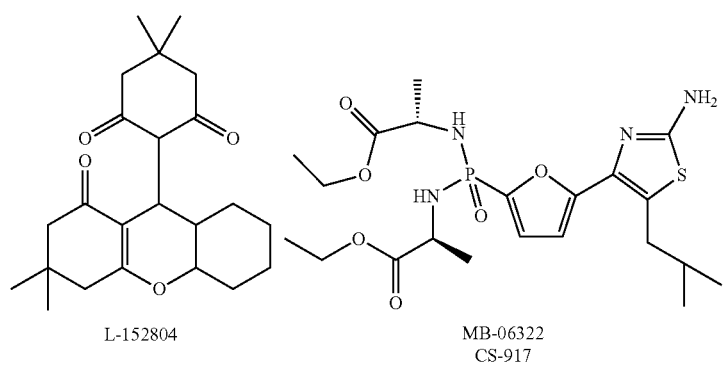
L-152804        MB-06322
               CS-917
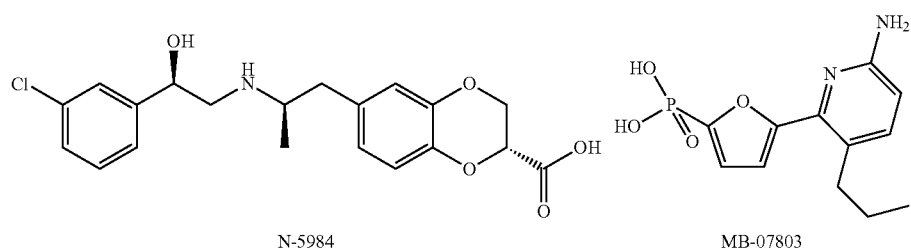
N-5984        MB-07803

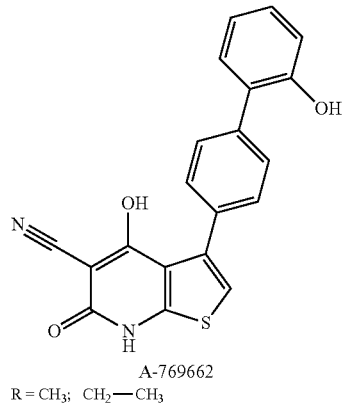

A-769662
R = CH₃; CH₂—CH₃

EXAMPLES

The examples and preparation methods adduced below serve to illustrate the invention, but without limiting it.

The inventive compounds of the formula I can be prepared with the aid of reactions known in principle. For example, the compounds were prepared according to the general reaction schemes which follow.

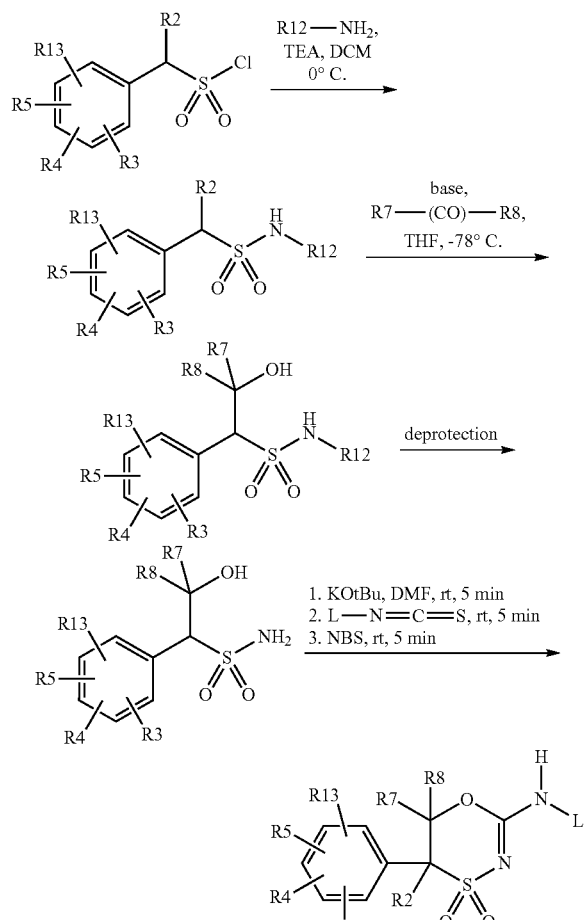

A methanesulfonyl chloride substituted by a phenyl radical and R2, through the reaction with a suitable amine and triethylamine (TEA) in a suitable solvent, for example dichloromethane (DCM), a corresponding phenyl- and R2-substituted methanesulfonamide protected by R12 (e.g. Boc, benzyl, 2,4-dimethoxybenzyl) is prepared. By reaction with a suitable base (e.g. methyllithium) at low temperature, it is then possible to produce a dianion, which reacts with a ketone (e.g. R7-(CO)—R8) or an aldehyde (e.g. R7-CHO) in a suitable solvent, e.g. tetrahydrofuran (THF), to give the R12-protected hydroxysulfonamide. By deprotection of R12 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with base and an isothiocyanate (L-N═C═S), and subsequent oxidative ring closure with N-bromosuccinimide (NBS), gives the desired 4,4-dioxooxathiazines.

In the cases in which the functional groups (for example a hydroxyl group) are introduced in protected form (for example benzyl-protected or as the ester), these are released at the end of the synthesis by a suitable method (for example hydrogenation or reduction).

The isothiocyanates used are obtained by the reaction of a primary amine with thiocarbonyldiimidazole, in which case any troublesome functional groups present, for example hydroxyl groups, are blocked with suitable protecting groups, for example silyl ethers. The protecting groups are removed at the end of the sequence by suitable methods, for example silyl groups by treatment with methanolic hydrochloric acid.

In the cases in which diastereomers or racemates form during the synthesis, these can be separated from one another by preparative HPLC.

Some of the primary amines used are commercially available.

4-Fluorobicyclo[2.2.2]octan-1-amine can be prepared as described in the literature (JOC 1982, 47, 1952-7).

Other inventive compounds can be obtained in other ways outlined by way of example in the scheme which follows.

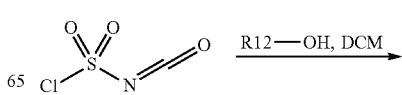

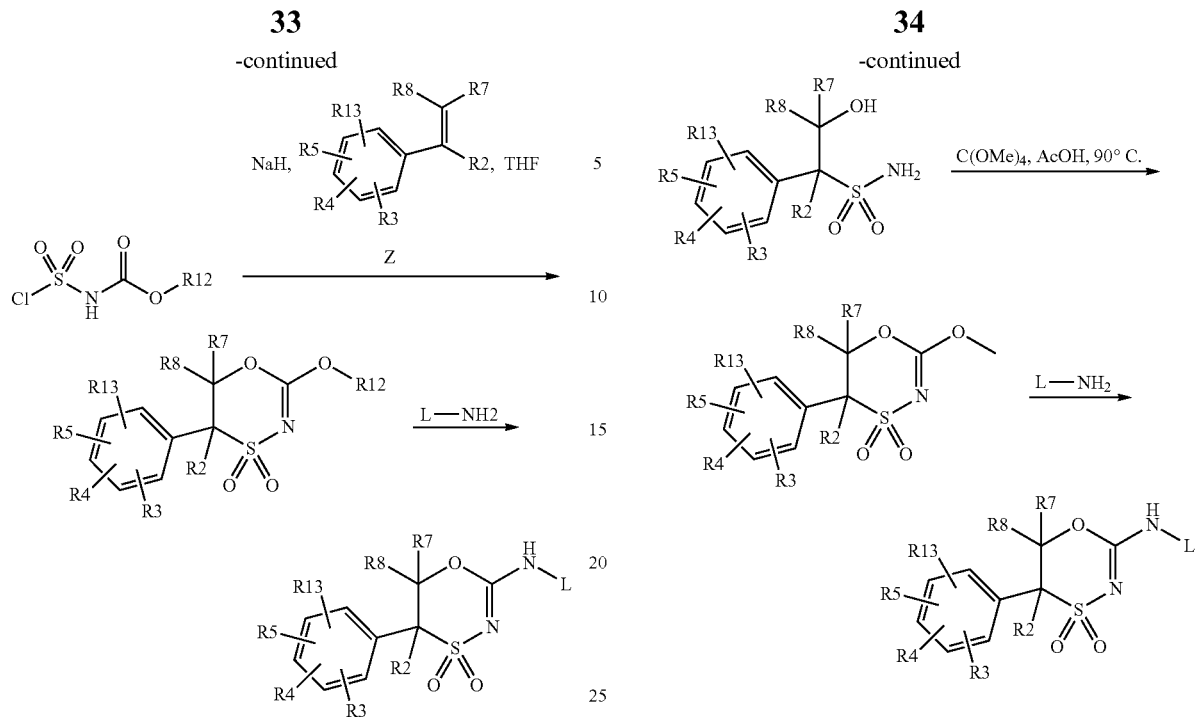

In analogy to a literature method (JACS 1972, 94, 4386-7), chlorosulfonyl isocyanate is treated with an alcohol (R12-OH, e.g. methanol), forming a corresponding carboalkoxysulfamoyl chloride (e.g. carbomethoxysulfamoyl chloride). This is deprotonated with sodium hydride, and the intermediate formed after chloride elimination (e.g. methyl-N-sulfonylurethane) reacts in a 2+4 cycloaddition with alkenes of the formula Z to give the alkoxy-substituted (e.g. methoxy-substituted) 4,4-dioxooxathiazine. The alkoxy group can be replaced here by means of an amine in a suitable solvent (e.g. dichloromethane), forming the desired 4,4-dioxooxathiazines.

In the cases in which diastereomers or racemates form during the synthesis, these can be separated from one another by preparative HPLC.

Other inventive compounds can be obtained in other ways outlined by way of example in the scheme which follows.

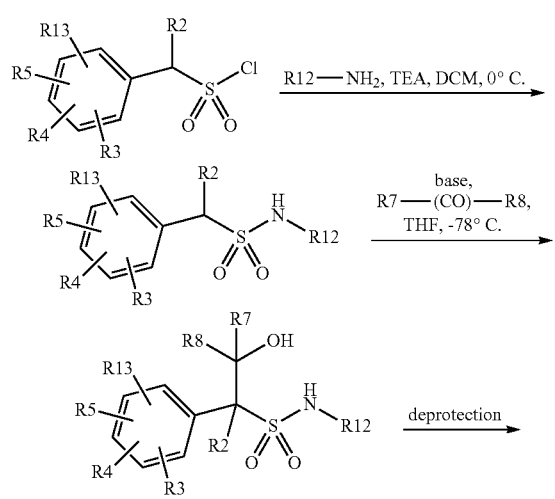

A methanesulfonyl chloride substituted by phenyl and R2, through the reaction with a suitable amine and triethylamine (TEA) in a suitable solvent, for example dichloromethane (DCM), a corresponding phenyl- and R2-substituted methanesulfonamide protected by R12 (e.g. Boc, benzyl, 2,4-dimethoxybenzyl) is prepared. By treatment with a suitable base (e.g. methyllithium) at low temperature, it is then possible to produce a dianion, which is reacted with a ketone (e.g. R7-(CO)—R8) or an aldehyde (e.g. R7-CHO) in a suitable solvent, e.g. tetrahydrofuran (THF), to give the R12-protected hydroxysulfonamide. By deprotection of R 12 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with tetramethyl orthocarbonate gives methoxy-substituted 4,4-dioxooxathiazines. The methoxy group (—O—$CH_3$) is then replaced by means of an amine (L-$NH_2$) in a suitable solvent (e.g. dichloromethane), forming the desired 4,4-dioxooxathiazines.

In the cases in which functional groups (for example a hydroxyl group) are introduced in protected form (for example benzyl-protected or as the ester), these are released at the end of the synthesis by a suitable method (for example hydrogenation or reduction).

If the molecule which forms includes a haloaryl unit, the halogen can be replaced by standard metal-catalyzed coupling methods. For example, a bromide can be converted further with the aid of a Suzuki reaction or a Sonogashira reaction or a palladium-catalyzed amination. In addition, simple synthesis steps may follow in some cases; for example, a triple bond can be hydrogenated to a single bond or a Boc-protected amine can be deprotected and then alkylated.

Some of the amines used are commercially available or can be prepared by methods known from the literature.

Others among the primary amines used were prepared as outlined in the scheme which follows.

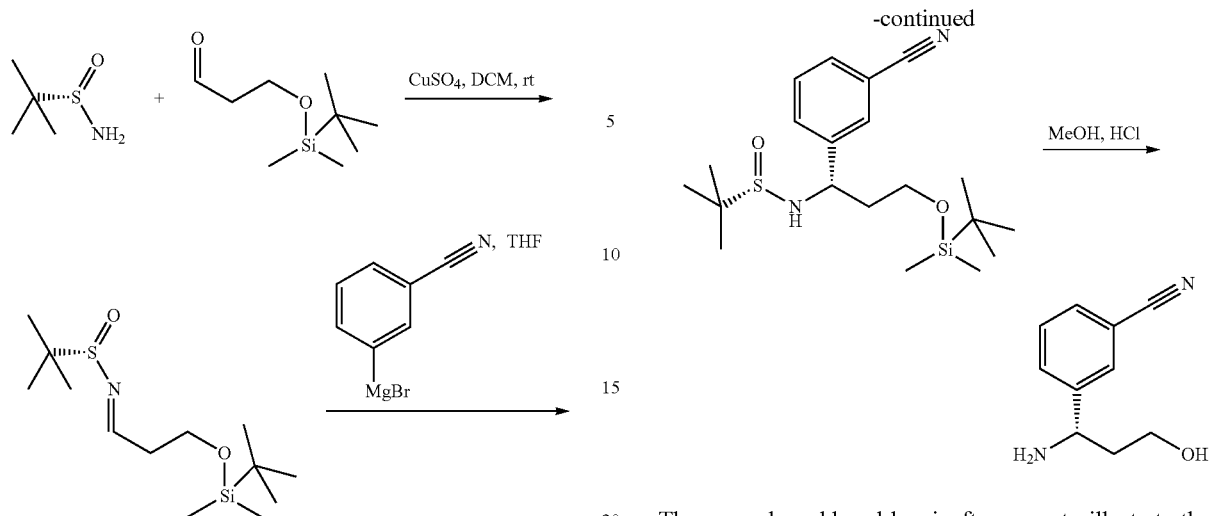
The examples adduced hereinafter serve to illustrate the invention, but without restricting it.
TABLE 1
| Example | CHEMISTRY | Method | Retention time | Molar weight (g/mol) |
|---|---|---|---|---|
| 1 | | C | 1.804 | 494.6 |
| 2 | | C | 1.432 | 553.7 |
| 3 | | C | 1.452 | 496.4 |
| 4 | | C | 1.59 | 493.6 |

TABLE 1-continued

| | | | | |
|---|---|---|---|---|
| 5 | [structure] | C | 1.118 | 596.7 |
| 6 | [structure] | C | 1.115 | 596.7 |

| Example | Name |
|---|---|
| 1 | 4'-[(S)-2-(Hexahydro-2,5-methanopentalen-3a-ylamino)-6,6-dimethyl-4,4-dioxo-5,6-dihydro-4H-4lambda6-[1,4,3]oxathiazin-5-yl]-biphenyl-3-carboxylic acid |
| 2 | ((S)-6,6-Dimethyl-4,4-dioxo-5-{4-[1-(3,3,3-trifluoropropyl)-piperidin-4-yl]phenyl}-5,6-dihydro-4H-4lambda6-[1,4,3]oxathiazin-2-yl)-(hexahydro-2,5-methanopentalen-3a-yl)amine |
| 3 | 3a-[(R)-5-(4-Bromophenyl)-6,6-dimethyl-4,4-dioxo-5,6-dihydro-4H-4lambda6-[1,4,3]oxathiazin-2-ylamino]hexahydro-2,5-methanopentalene-2-carboxamide* |
| 4 | 3a-((R)-5-Biphenyl-4-yl-6,6-dimethyl-4,4-dioxo-5,6-dihydro-4H-4lambda6-[1,4,3]oxathiazin-2-ylamino)hexahydro-2,5-methane-pentalene-2-carboxamide* |
| 5 | 3a-((R)-6,6-Dimethyl-4,4-dioxo-5-{4-[1-(3,3,3-trifluoropropyl)piperidin-4-yl]phenyl}-5,6-dihydro-4H-4lambda6-[1,4,3]oxathiazin-2-ylamino)hexahydro-2,5-methane-pentalene-2-carboxamide* |
| 6 | 3a-((S)-6,6-Dimethyl-4,4-dioxo-5-{4-[1-(3,3,3-trifluoropropyl)piperidin-4-yl]phenyl}-5,6-dihydro-4H-4lambda6-[1,4,3]oxathiazin-2-ylamino)hexahydro-2,5-methane-pentalene-2-carboxamide* |

*diastereomer mixture

Chromatography Methods
Method A
LC UV/MS: Agilent 1200 Series
Column: Mercury MS, Luna C18(2), S-3 µm, 10×2.0 mm
Eluent: 0 min 93% $H_2O$ (0.05% II-A)-1.0 min 95% acetonitrile-1.45 min 95% acetonitrile-1.5 min 7% acetonitrile (30° C., flow rate 1.1 ml/min)
Method B
LC UV/MS: Agilent 1100 Series
Column: Mercury MS, Luna C18(2), S-3 µm, 10×2.0 mm
Eluent: 0 min 93% $H_2O$ (0.05% TFA)-1.2 min 95% acetonitrile-1.4 min 95% acetonitrile-1.45 min 7% acetonitrile (30° C., flow rate 1.1 ml/min)
Method C
LC UV/MS: Agilent 1100 Series
Column: YMC J'spere ODS H80, 80 Å, S-4 µm, 20×2.1 mm
Eluent: 0 min 96% $H_2O$ (0.05% TFA)-2.0 min 95% acetonitrile-2.4 min 95% acetonitrile-2.45 min 4% acetonitrile (30° C., flow rate 1 ml/min)

The efficacy of the compounds was tested as follows:
Enzymatic 11Beta-HSD1 Test:

To measure the activity of the compounds, an SPA-based detection method (Solly et al. 2005) was employed. First of all, 20 µl of the human 11β-HSD1 microsome fraction (0.2 µg of protein), prepared in 50 mM HEPES, 0.1% BSA (w/v), were applied to a plate with 384 wells. The test compounds (0.09 µl) were applied to the assay plate in 100% DMSO. The reaction was started by addition of 20 µl of [1,2-$^3$H]-cortisone (0.1 µCi/100 mM) in assay buffer comprising 25 mM HEPES, 100 mM KCl, 5 mM NaCl, 2 mM $MgCl_2$ and 0.25 mM NADPH. The plate was agitated at 37° C. for 1 hour. At the same time, a stop solution comprising 20 mg/ml SPA-PVT beads, 1.6 mg/ml monoclonal cortisol antibody and 0.01 mM SSR110887 (inhibitor from the Biovitrium patent) in 50 mM HEPES, 1 M NaCl and 1 M KCl was stirred at room temperature. To stop the reaction, 25 μl of the stop solution were added to each well. The plate was agitated gently at room temperature for 1 further hour and then centrifuged at 500 $g_{av}$ for 1 minute, in order that the SPA beads could settle out. The plate was then read in a Wallac-1450-Microbeta unit with a standard SPA program (counting time 1 min/well). The comparative compound was glycyrrhetinic acid.

Protein and radioactive substrate were dispensed with a Biomek FX unit (Beckman Coulter) for handling liquids. The test compounds were added with a Cybi-Well equipped with a 90 nl pin tool (CyBio).

Lit.: Solly S, Mundt S S, Zokian H J, Juy-Fang Ding G, Hermanowski-Vosatka A, Strulovici B and Zheng W. High-throughput screening of 11β-Hydroxysteroid dehydrogenase type 1 in scintillation proximity format. Assay Drug Dev Technol 2005; 3:377-384.

TABLE 2

| Biological activity | |
| --- | --- |
| Example | $IC_{50}$ (nM) |
| 1 | 14 |
| 2 | 24 |
| 3 | 22 |
| 4 | 34 |
| 5 | |
| 6 | |

It can be inferred from the test data that the compounds of the formula I inhibit 11beta-HSD1 (11beta-hydroxysteroid dehydrogenase type 1), and are thus of good suitability for treatment of hyperglycemia, insulin resistance, diabetes, obesity, lipid metabolism disorders and other diseases.

The preparation of some examples is described in detail hereinafter; the remaining compounds of the formula I were obtained analogously:

EXPERIMENTAL

C-(4-Bromophenyl)-N-(2,4-dimethoxybenzyl)methanesulfonamide

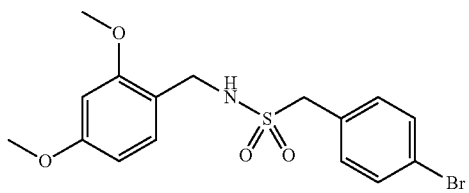 [SMILES: COc1ccc(CNS(=O)(=O)Cc2ccc(Br)cc2)c(OC)c1]

While cooling with ice, 20.0 g of 4-bromobenzylsulfonyl chloride were initially charged in 200 ml of dichloromethane, and a solution of 24 ml of 2,4-dimethoxybenzylamine in 100 ml of dichloromethane was slowly added dropwise. For improved stirrability, a further 100 ml of dichloromethane were added, and the reaction mixture was allowed to come to room temperature. After stirring for 2 hours, the reaction mixture was washed with 100 ml of water, with 100 ml of 0.2 N aqueous hydrochloric acid, with 100 ml of saturated aqueous sodium hydrogencarbonate solution and finally once more with 100 ml of water. The organic phase was dried over $Na_2SO_4$, concentrated by rotary evaporation and dried under high vacuum. The residue (30 g) was used in the next reaction without further purification.

N-(2,4-Dimethoxybenzyl)-1-(4-bromophenyl)-2-hydroxy-2-methylpropane-1-sulfonamide

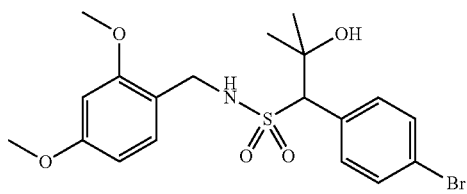 [SMILES: COc1ccc(CNS(=O)(=O)C(c2ccc(Br)cc2)C(C)(C)O)c(OC)c1]

Under inert gas, 28 g of C-(4-bromophenyl)-N-(2,4-dimethoxybenzyl)methanesulfonamide were initially charged in 250 ml of THF, and then, at a temperature of −78° C., 93 ml of a 1.6 N methyllithium solution in hexane were added dropwise and the mixture was left to stir while cooling with ice for 5 minutes. Subsequently, the reaction solution was cooled again to −78° C. and 20 ml of acetone were added. The mixture was allowed to come to room temperature and stirred for 30 minutes. The reaction solution was admixed with 13 ml of trifluoroacetic acid and 500 ml of ethyl acetate, and washed with 300 ml of a saturated aqueous sodium hydrogencarbonate solution and 300 ml of a saturated aqueous sodium chloride solution, and the organic phase was dried over $Na_2SO_4$ and concentrated by rotary evaporation. The residue was used in the next reaction without further purification.

1-(4-Bromophenyl)-2-hydroxy-2-methylpropane-1-sulfonamide

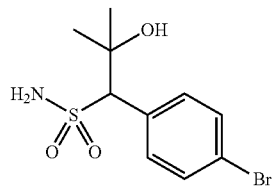

A solution of N-(2,4-dimethoxybenzyl)-1-(4-bromophenyl)-2-hydroxy-2-methylpropane-1-sulfonamide from the above reaction in 150 ml of dichloromethane was admixed with 50 ml of trifluoroacetic acid and stirred at room temperature for 17 hours. The starting solution was coevaporated twice with 100 ml of toluene and the crude product was purified using a Flashmaster with an n-heptane/ethyl acetate gradient by means of normal phase chromotography. The product-containing fractions were combined and concentrated by rotary evaporation. This gave the product (16 g) with a molecular weight of 308.2 g/mol ($C_{10}H_{14}BrNO_3S$).

5-(4-Bromophenyl)-2-methoxy-6,6-dimethyl-5,6-dihydro-[1,4,3]oxathiazine 4,4-dioxide

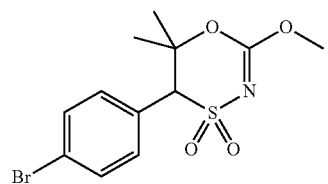 [SMILES: COC1=NS(=O)(=O)C(c2ccc(Br)cc2)C(C)(C)O1]

A mixture of 500 mg of 1-(4-bromophenyl)-2-hydroxy-2-methylpropane-1-sulfonamide in 2 ml of tetramethoxymethane and 0.5 ml of acetic acid was stirred at 100° C. for 3 hours. After the removal of the solvent under reduced pressure, the residue (565 mg) was used in the next reaction without further purification.

The compound can be separated by chiral chromatography into the enantiomers, (R)-5-(4-bromophenyl)-2-methoxy-6,6-dimethyl-5,6-dihydro-[1,4,3]oxathiazine 4,4-dioxide and (S)-5-(4-bromophenyl)-2-methoxy-6,6-dimethyl-5,6-dihydro-[1,4,3]oxathiazine 4,4-dioxide.

4'-[(S)-2-(Hexahydro-2,5-methanopentalen-3a-ylamino)-6,6-dimethyl-4,4-dioxo-5,6-dihydro-4H-4lambda*6*-[1,4,3]oxathiazin-5-yl]-biphenyl-3-carboxylic acid

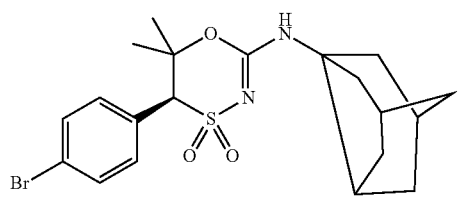 [SMILES: CC1(C)OC(NC23CC4CC(CC2C4)C3)=NS(=O)(=O)[C@H]1c1ccc(Br)cc1]

A solution of 411 mg of (S)-5-(4-bromophenyl)-2-methoxy-6,6-dimethyl-5,6-dihydro-1,4,3-oxathiazine 4,4-dioxide and 270 mg of 3-noradamantanamine (170 mg) in 5 ml of methylene chloride was concentrated by rotary evaporation and the residue was left to stand at room temperature overnight. The crude product was purified by means of normal phase chromatography using a Flashmaster with an n-heptane/ethyl acetate gradient. The product-containing fractions were combined and concentrated by rotary evaporation. This gave the product (431 mg) with a molecular weight of 453.4 g/mol ($C_{20}H_{25}BrN_2O_3S$).

4'-[(S)-2-(Hexahydro-2,5-methanopentalen-3a-ylamino)-6,6-dimethyl-4,4-dioxo-5,6-dihydro-4H-4lambda*6*-[1,4,3]oxathiazin-5-yl]-biphenyl-3-carboxylic acid

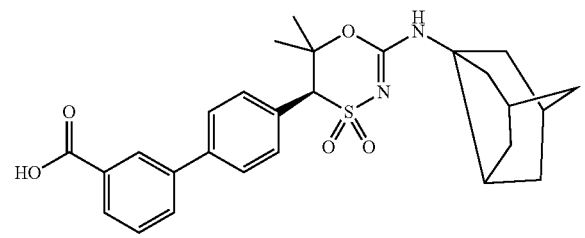 [SMILES: CC1(C)OC(NC23CC4CC(CC2C4)C3)=NS(=O)(=O)[C@H]1c1ccc(-c2cccc(C(=O)O)c2)cc1]

Under inert gas, 40 mg of CTC-Q-PHOS were added to a mixture of 79 mg of 3-carboxyphenylboronic acid, 150 mg of 4'-[(S)-2-(hexahydro-2,5-methanopentalen-3a-ylamino)-6,6-dimethyl-4,4-dioxo-5,6-dihydro-4H-4lambda*6*-[1,4,3]oxathiazin-5-yl]-biphenyl-3-carboxylic acid and 380 mg of cesium carbonate in 3 ml of dioxane and 1 ml of water. After stirring at 62° C. for 40 minutes, the reaction was allowed to cool to room temperature, 50 ml of ethyl acetate were added and the organic phase was washed with 20 ml of water and 20 ml of saturated aqueous sodium chloride solution. The organic phase was dried over MgSO$_4$ and concentrated by rotary evaporation. The crude product was purified by means of normal phase chromatography using a Flashmaster with an n-heptane/ethyl acetate gradient. The product-containing fractions were combined and concentrated by rotary evaporation. The crude product was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO$_4$ and concentrated by rotary evaporation, and the residue was taken up again in a mixture of acetonitrile and water and lyophilized. This gave the product (49 mg) with a molecular weight of 494.6 g/mol ($C_{27}H_{30}N_2O_5S$); MS (ESI): m/e=495 (M+H$^+$).

In an analogous manner, the following products were obtained:

3a-[(R)-5-(4-Bromophenyl)-6,6-dimethyl-4,4-dioxo-5,6-dihydro-4H-4lambda*6*-[1,4,3]oxathiazin-2-ylamino]hexahydro-2,5-methanopentalene-2-carboxamide

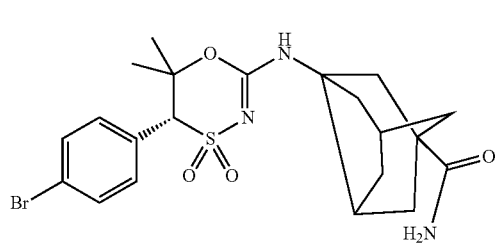 [SMILES: CC1(C)OC(NC23CC4CC2CC(C(N)=O)(C4)C3)=NS(=O)(=O)[C@@H]1c1ccc(Br)cc1]

3a-((R)-5-Biphenyl-4-yl-6,6-dimethyl-4,4-dioxo-5,6-dihydro-4H-4lambda*6*-[1,4,3]oxathiazin-2-ylamino)hexahydro-2,5-methanopentalene-2-carboxamide

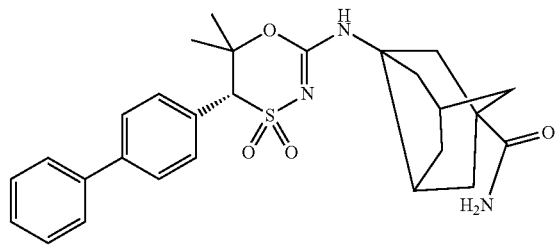 [SMILES: CC1(C)OC(NC23CC4CC2CC(C(N)=O)(C4)C3)=NS(=O)(=O)[C@@H]1c1ccc(-c2ccccc2)cc1]

4-{4-[(R)-2-(2-Carbamoylhexahydro-2,5-methanopentalen-3a-ylamino)-6,6-dimethyl-4,4-dioxo-5,6-dihydro-4H-4lambda*6*-[1,4,3]oxathiazin-5-yl]phenyl}-3,6-dihydro-2H-pyridine-1-carboxylic acid butyl ester

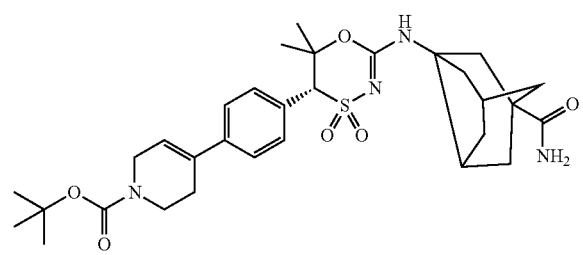 [SMILES: CC(C)(C)OC(=O)N1CC=C(c2ccc([C@@H]3C(C)(C)OC(NC45CC6CC4CC(C(N)=O)(C6)C5)=NS3(=O)=O)cc2)CC1]

A solution of N-boc-4-(4,4,5,5-tetramethyl-[1,3,2]dioxaborolan-2-yl)-3,6-dihydro-2H-pyridine (112 mg), cesium carbonate (212 mg) and 3a-[(R)-5-(4-bromophenyl)-6,6- dimethyl-4,4-dioxo-5,6-dihydro-4H-4lambda*6*-[1,4,3]oxathiazin-2-ylamino]hexahydro-2,5-methanopentalene-2-carboxamide (150 mg) in dioxane (2 ml)/water (1 ml) was purged with argon for twenty minutes. Then CTC-Q-PHOS (43 mg) and bis(dibenzylideneacetone)palladium (17 mg) were added and the mixture was stirred at 65° C. for thirty minutes. Subsequently, ethyl acetate (20 ml) was added and the mixture was washed with water (10 ml). The organic phase was dried using a kieselguhr cartridge, filtered and concentrated under reduced pressure. This was followed by purification by column chromatography (ethyl acetate/heptane). This gave the product (140 mg) with a molecular weight of 598.8 g/mol ($C_{31}H_{42}N_4O_6S$).

3a-[(R)-6,6-Dimethyl-4,4-dioxo-5-(4-piperidin-4-yl-phenyl)-5,6-dihydro-4H-4lambda*6*-[1,4,3]oxathiazin-2-ylamino]hexahydro-2,5-methanopentalene-2-carboxamide

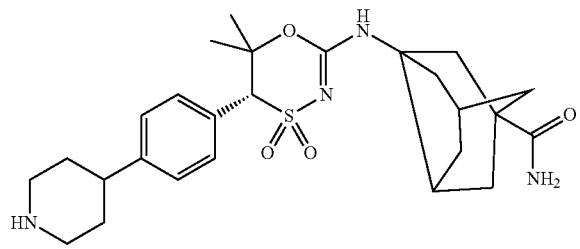 [SMILES: CC1(C)OC(NC23CC4CC2CC(C(N)=O)(C4)C3)=NS(=O)(=O)[C@@H]1c1ccc(C2CCNCC2)cc1]

A solution of 4-{4-[(R)-2-(2-carbamoylhexahydro-2,5-methanopentalen-3a-ylamino)-6,6-dimethyl-4,4-dioxo-5,6-dihydro-4H-4lambda*6*-[1,4,3]oxathiazin-5-yl]-phenyl}-3,6-dihydro-2H-pyridine-1-carboxylic acid butyl ester (100 mg) in methanol (10 mL) was admixed with palladium on carbon (10%, 100 mg) and the mixture was stirred in a hydrogen atmosphere for 1.5 h. The mixture was filtered and concentrated. The residue was dissolved in 5 mL of dichloromethane, and 1 mL of trifluoroacetic acid was added. After stirring at room temperature for 1 h, the solvent was removed under reduced pressure and TFA ester formed was cleaved by treatment with 1 N HCl. Extraction with ethyl acetate gave the crude product, which was used without further purification.

3a-((R)-6,6-Dimethyl-4,4-dioxo-5-{4-[1-(3,3,3-trifluoropropyl)piperidin-4-yl]-phenyl}-5,6-dihydro-4H-4lambda*6*-[1,4,3]oxathiazin-2-ylamino)-hexahydro-2,5-methanopentalene-2-carboxamide

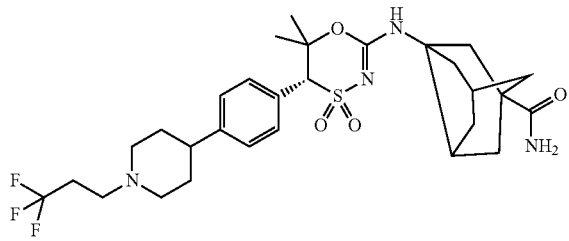 [SMILES: CC1(C)OC(NC23CC4CC2CC(C(N)=O)(C4)C3)=NS(=O)(=O)[C@@H]1c1ccc(C2CCN(CCC(F)(F)F)CC2)cc1]

DIPEA (75 mg) and 3-bromo-1,1,1-trifluoropropane (500 mg) were added to a solution of 3a-[(R)-6,6-dimethyl-4,4-dioxo-5-(4-piperidin-4-yl-phenyl)-5,6-dihydro-4H-4lambda*6*-[1,4,3]oxathiazin-2-ylamino]hexahydro-2,5-methanopentalene-2-carboxamide (73 mg) in DMF (1.5 mL), and the mixture was stirred overnight. The resulting mixture was purified in a purification laboratory by means of preparative HPLC. This gave the product with a molecular weight of 596.7 g/mol ($C_{29}H_{39}F_3N_4O_4S$); MS (ESI): m/e=597 ($M+H^+$).

In an analogous manner, the following products were obtained:

3a-((S)-6,6-Dimethyl-4,4-dioxo-5-{4-[1-(3,3,3-trifluoropropyl)piperidin-4-yl]phenyl}-5,6-dihydro-4H-4lambda*6*-[1,4,3]oxathiazin-2-ylamino)hexahydro-2,5-methanopentalene-2-carboxamide

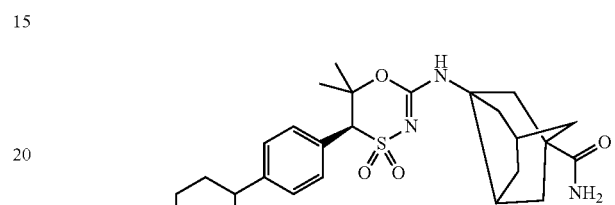

((S)-6,6-Dimethyl-4,4-dioxo-5-{4-[1-(3,3,3-trifluoropropyl)piperidin-4-yl]phenyl}-5,6-dihydro-4H-4lambda*6*-[1,4,3]oxathiazin-2-yl)-(hexahydro-2,5-methanopentalen-3a-yl)amine

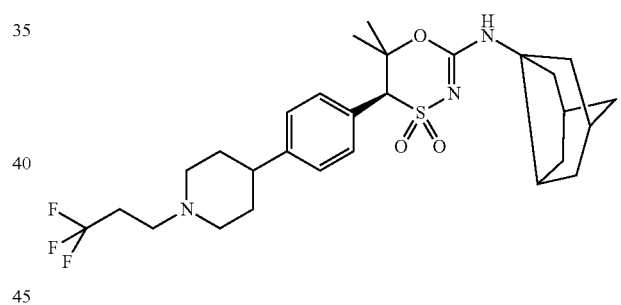

5-Phenyladamantan-2-one

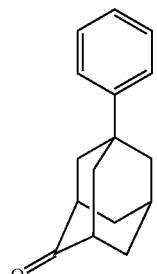

WO20071113634A1 discloses the chemical reaction, but the workup (crystallization) was optimized here. The reaction thus gives the product in greater purity at comparable yield.

(3R,7R)-5-Hydroxyadamantan-2-one (25 g) was dissolved in benzene (200 ml). Trifluormethanesulfonic acid (13.1 ml)

was added in such a way that the reaction stirred at room temperature. Subsequently, the reaction was stirred at reflux. After again adding trifluoromethanesulfonic acid (2 ml), the reaction was stirred again at reflux. After adding tert-butyl methyl ether, the mixture was washed repeatedly with water. After filtration, the resulting solution was fully concentrated. The residue was taken up in n-heptane, hot-filtered and then crystallized. This gave 5-phenyladamantan-2-one (26.9 g) as a white solid.

2-Methyl-5-phenyladamantan-2-ol

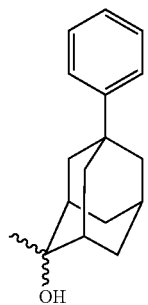

A preparation is described in WO2007/113634A1. The method described here is safer, since the direct handling of methylmagnesium bromide/chloride is avoided. The Grignard reagent is formed in situ. This considerably facilitates larger batches (on the laboratory scale).

5-Phenyladamantan-2-one (301 g) was dissolved in a mixture of THF (4.251) and tert-butyl methyl ether (850 ml). After addition of iodomethane (566 g), magnesium (97 g) was added. The reaction was subsequently stirred until conversion was complete, while not exceeding a te2.5 Imperature of 55° C. Completion of conversion was followed by dilution with tert-butyl methyl ether (3 l) and water (300 ml). Addition of hydrochloric acid (32%) set a pH of pH2. After again adding water and subsequently separating the phases, the organic phase was extracted repeatedly with water. The organic solution was clarified with activated carbon and then concentrated fully under reduced pressure. This gave 2-methyl-5-phenyladamantan-2-ol (312.2 g) as an oil.

1-(2-Phenylhexahydro-2,5-methanopentalen-3a-yl) ethanone

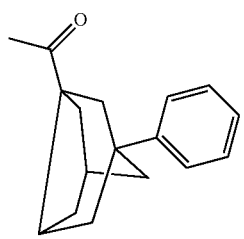 [SMILES: CC(=O)C12CC3CC1CC(c1ccccc1)(C3)C2]

The reaction is described in WO2007/113634A1 with poorer yield (59% vs. 98%).

A solution of 2-methyl-5-phenyladamantan-2-ol (300 g) in THF (710 ml) and acetic acid (160 ml) was added at 0° C. to a solution (8.3%, 3330 ml) of sodium hypochloride in water. After addition of n-tetrabutylammonium iodide (25.6 g), the mixture was heated to 25° C. within 90 minutes. After full conversion and phase separation, the organic phase was washed repeatedly with water. After full concentration of the organic phase, the residue was taken up in methanol (525 ml). Potassium hydroxide (82 g) was added and the mixture was stirred at room temperature. After adding tert-butyl methyl ether, the mixture was washed repeatedly with water. The organic solution was clarified with activated carbon and concentrated fully under reduced pressure. This gave 1-(2-phenylhexahydro-2,5-methanopentalen-3a-yl)ethanone (320 g) as an oil.

2-Phenylhexahydro-2,5-methanopentalene-3a-carboxylic acid

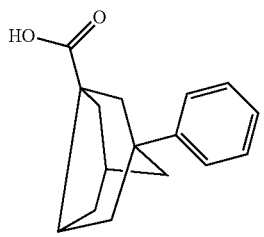 [SMILES: O=C(O)C12CC3CC1CC(c1ccccc1)(C3)C2]

The reaction is described in WO2007/113634A1 with poorer yield (64% vs. 89%).

Dioxane (1.81) was added to a solution, cooled to −22° C., of sodium hydroxide (724 g) in water (4.8 l). Bromine (578 g) was metered into this solution such that a temperature of −15° C. was not exceeded. A solution of 1-(2-phenylhexahydro-2, 5-methanopentalen-3a-yl)ethanone (290 g) in dioxane (600 ml) was metered into this solution, and the reaction was allowed to warm up gradually to room temperature. tert-Butyl methyl ether was added. Subsequently, water was metered in (2.5 l). After phase separation, the aqueous phase was washed with tert-butyl methyl ether. Subsequently, after addition of tert-butyl methyl ether (5 l), hydrochloric acid (32%) was used to establish a pH of pH 1.5. After phase separation, the organic phase was washed repeatedly with water and clarified with activated carbon. The solvent was changed by distillation under reduced pressure with addition of diisopropyl ether. After extractive stirring with diisopropyl ether at reflux, 2-phenylhexahydro-2,5-methanopentalene-3a-carboxylic acid (292 g) was obtained as a solid with 95% purity.

(2-Phenylhexahydro-2,5-methanopentalen-3a-yl) carbamic acid tert-butyl ester

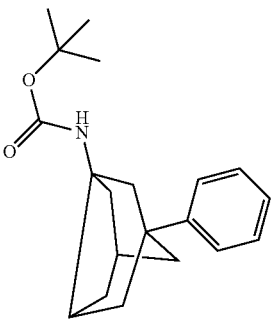 [SMILES: CC(C)(C)OC(=O)NC12CC3CC1CC(c1ccccc1)(C3)C2]

2-Phenylhexahydro-2,5-methanopentalen-3a-carboxylic acid (50 g) was dissolved in t-butanol (1 l), and triethylamine (51 g) was added to this solution. Diphenylphosphoryl azide (56 g) was added in portions at room temperature. The reaction was stirred first at room temperature and then at reflux. After removal of the t-butanol, the residue was taken up in water (800 ml). The precipitated solids were filtered off and washed repeatedly with water. After drying under reduced pressure, the solids were taken up in tert-butyl methyl ether. This forms a solid, which was filtered off. The filtrate was concentrated fully under reduced pressure and then stirred with diisopropyl ether. The solids were filtered off with suction and washed with a mixture of diisopropyl ether and n-heptane. After drying, (2-phenylhexahydro-2,5-methanopentalen-3a-yl)carbamic acid tert-butyl ester (83.9 g) was obtained.

3a-tert-Butoxycarbonylaminohexahydro-2,5-methanopentalen-2-carboxylic acid

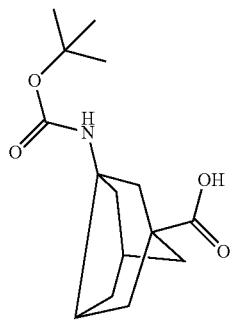

(2-Phenylhexahydro-2,5-methanopentalen-3a-yl)carbamic acid tert-butyl ester (12 g) was initially charged in acetonitrile (240 ml), carbon tetrachloride (240 ml) and water (360 ml), then ruthenium chloride (0.4 g) was added. Subsequently, sodium periodate (120 g) was metered in in portions. The reaction was stirred further at room temperature and then diluted with tert-butyl methyl ether. After phase separation, the organic phase was washed repeatedly with water and then extracted with sodium hydroxide solution (0.1 M, 100 ml). Subsequently, the aqueous phase was washed with tert-butyl methyl ether and then set to a pH of pH 3-4 with hydrochloric acid (0.5 M) in the presence of tert-butyl methyl ether. After phase separation, the organic phase was washed repeatedly with water and then concentrated fully under reduced pressure. The residue was stirred with a mixture of acetonitrile and diisopropyl ether. After filtration with suction and drying, 3a-tert-butoxycarbonylaminohexahydro-2,5-methanopentalene-2-carboxylic acid (6.6 g) was obtained as a white solid.

(2-Carbamoylhexahydro-2,5-methanopentalen-3a-yl)carbamic acid tert-butyl ester

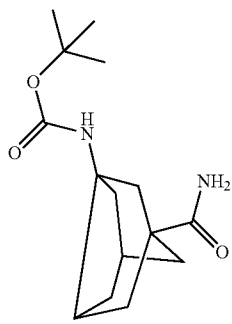 [SMILES: CC(C)(C)OC(=O)NC12CC3CC1CC(C(N)=O)(C3)C2]

3a-tert-Butoxycarbonylaminohexahydro-2,5-methanopentalene-2-carboxylic acid was dissolved in DMF (200 ml), and DIPEA (10.6 g) and ammonia (6.1 ml, 7M in MeOH) were added. Subsequently, HATU (14.8 g) was added and the mixture was stirred at room temperature for 2 h. The reaction solution was concentrated by rotary evaporation down to volume 50 ml, poured into 400 ml of dilute NaHCO$_3$ solution (300 ml of H$_2$O+100 ml of saturated NaHCO$_3$ solution) and extracted 3 times with 100 ml of EtOAc. Then dried over MgSO$_4$, filtered and concentrated by rotary evaporation.

Residue dissolved in DMF and purified by means of inverse phase (Biotage). The fractions of value were combined, acetonitrile was evaporated off and the aqueous residue was freeze-dried. The residue (1.81 g) was used further without further workup.

3a-Aminohexahydro-2,5-methanopentalene-2-carboxamide

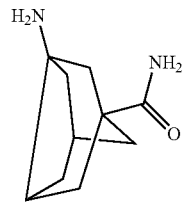

(2-Carbamoylhexahydro-2,5-methanopentalen-3a-yl)carbamic acid tert-butyl ester (1.8 g) dissolved in dichloromethane (50 ml), 11 equivalents of HCl (4M in dioxane) added and the mixture stirred at room temperature overnight. LCMS: amine is fully deprotected. The reaction solution was concentrated by rotary evaporation, the HCl salt of the amine was released with 50 ml of saturated Na$_2$CO$_3$ solution+3 ml of 2M NaOH, and the mixture was extracted a total of 8 times with 20 ml of dichloromethane and once with EtOAc. The organic solutions were combined, dried over MgSO$_4$, filtered, concentrated by rotary evaporation and dried under high vacuum. The residue (0.91 g) was used further without further workup.

The invention claimed is:
1. A compound of the formula I

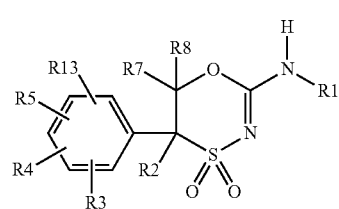

in which
R1
    is

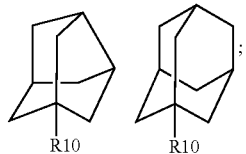

R2 is H, F, (C$_1$-C$_3$)-alkyl where the alkyl radical may be mono- to trisubstituted by fluorine;

49

R3, R4, R5, R13 are each independently
  H, F, Cl, Br, I, OH, $CF_3$, $CHF_2$, $CH_2F$, $NO_2$, CN, $OCF_3$, $OCHF_2$, —$(C_1-C_6)$-alkylene-(R9), O—$(C_1-C_6)$-alkylene-(R9), tert-butyl, isopropylene-(R9), (C=O)—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-R9$)_2$, $(C_1-C_6)$-alkylene-$NH_2$, $(C_1-C_6)$-alkylene-$NH(C_1-C_6)$-alkylene-(R9), $(C_1-C_6)$-alkylene-$N((C_1-C_6)$-alkylene-R9$)_2$, —O—$(C_1-C_6)$-alkylene-$NH_2$, —O—$(C_1-C_6)$-alkylene-$NH(C_1-C_6)$-alkylene-(R9), —O—$(C_1-C_6)$-alkylene-$N((C_1-C_6)$-alkylene-R9$)_2$, —NH—$(C_1-C_6)$-alkylene-$NH_2$, —NH—$(C_1-C_6)$-alkylene-$NH(C_1-C_6)$-alkylene-(R9), —NH—$(C_1-C_6)$-alkylene-$N((C_1-C_6)$-alkylene-R9$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
  $(C_6-C_{10})$-aryl, —$(C_1-C_6)$-alkylene-$(C_6-C_{10})$-aryl,
    where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$C_1-C_6$)-alkyl, $CONH_2$, $CONH(C_1-C_6)$-alkyl, $CON((C_1-C_6)$-alkyl$)_2$, $SF_5$, $(C_6-C_{10})$-aryl, $(C_3-C_7)$-cycloalkyl, 4- to 12-membered heterocycle;
      where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
  4- to 12-membered heterocycle, —$(C_1-C_6)$-alkylene-4- to -12-membered heterocycle,
    where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$, $(C_6-C_{10})$-aryl, $(C_3-C_7)$-cycloalkyl, 4- to 12-membered heterocycle;
      where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
R7, R8 are each independently H, $(C_1-C_3)$-alkyl, where the alkyl radical may be mono- to trisubstituted by fluorine, or R7 and R8 together with the carbon atom to which they are bonded form a 3-7-membered carbocycle or heterocycle;

50

R9 is H, OH, $OCH_3$, $OCF_3$, $CHF_2$, $CF_3$;
R10 is H, $CONH_2$;
and pharmaceutically compatible salts thereof.

2. The compound of claim 1, wherein
R1 is

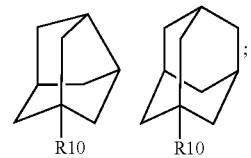

R2 is H, $(C_1-C_3)$-alkyl;
R3, R4, R5, R13 are each independently
  H, F, Cl, Br, I, OH, $CF_3$, $CHF_2$, $CH_2F$, $NO_2$, CN, $OCF_3$, $OCHF_2$, —$(C_1-C_6)$-alkylene-(R9), O—$(C_1-C_6)$-alkylene-(R9), tert-butyl, isopropylene-(R9), (C=O)—$(C_1-C_6)$-alkylene-(R9), $(C_1-C_6)$-alkylene-(R9), $NH_2$, $NH(C_1-C_6)$-alkylene-(R9), $N((C_1-C_6)$-alkylene-R9$)_2$, $(C_1-C_6)$-alkylene-$NH_2$, $(C_1-C_6)$-alkylene-$NH(C_1-C_6)$-alkylene-(R9), $(C_1-C_6)$-alkylene-$N((C_1-C_6)$-alkylene-R9$)_2$, —O—$(C_1-C_6)$-alkylene-$NH_2$, —O—$(C_1-C_6)$-alkylene-$NH(C_1-C_6)$-alkylene-(R9), —O—$(C_1-C_6)$-alkylene-$N((C_1-C_6)$-alkylene-R9$)_2$, —NH—$(C_1-C_6)$-alkylene-$NH_2$, —NH—$(C_1-C_6)$-alkylene-$NH(C_1-C_6)$-alkylene-(R9), —NH—$(C_1-C_6)$-alkylene-$N((C_1-C_6)$-alkylene-R9$)_2$, $SO_2$—$CH_3$, $SO_2$—$NH_2$, $SO_2$—$NH(C_1-C_6)$-alkyl, $SO_2$—$N((C_1-C_6)$-alky$)_2$, COOH, COO—$(C_1-C_6)$-alkyl, $CONH_2$, $CONH(C_1-C_6)$-alkyl, CON$((C_1-C_6)$-alkyl$)_2$, $SF_5$;
  $(C_6-C_{10})$-aryl, —$(C_1-C_6)$-alkylene-$(C_6-C_{10})$-aryl,
    where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$, $(C_6-C_{10})$-aryl, $(C_3-C_7)$-cycloalkyl, 4- to 12-membered heterocycle;
      where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
  4- to 12-membered heterocycle, —$(C_1-C_6)$-alkylene-4- to -12-membered heterocycle,
    where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$—$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$, $(C_6-C_{10})$-aryl, $(C_3-C_7)$-cycloalkyl, 4- to 12-membered heterocycle;

where the $(C_6-C_{10})$-aryl radical, $(C_3-C_7)$-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;

R7, R8 are each independently H, $(C_1-C_3)$-alkyl;
R9 is H, OH, $OCH_3$, $OCF_3$, $CHF_2$, $CF_3$;
R10 is H, $CONH_2$;
and pharmaceutically compatible salts thereof.

3. The compound of claim 1, wherein
R1
is

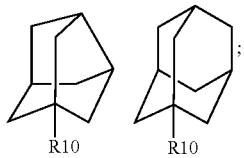

R2 is H;
R3, R4, R5, R13 are each independently
H, F, Cl, Br, I, OH, $CF_3$, $NO_2$, CN, $OCF_3$, $OCHF_2$, —$(C_1-C_6)$-alkylene, —O—$(C_1-C_6)$-alkylene;
$(C_6-C_{10})$-aryl,
where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
4- to 12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$—$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$;
R7, R8 is H, $(C_1-C_3)$-alkyl;
R9 is H, OH, $OCH_3$, $OCF_3$, $CHF_2$, $CF_3$;
R10 is H, $CONH_2$;
and pharmaceutically compatible salts thereof.

4. The compound of claim 1, wherein
R1
is

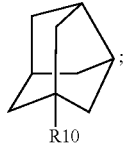

R2 is H;
R3, R4, R5 are each independently
H, F, Cl, Br, I, OH, $CF_3$, $NO_2$, CN, $OCF_3$, $OCHF_2$, —$(C_1-C_6)$-alkylene, —O—$(C_1-C_6)$-alkylene;
phenyl,
where the phenyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_{1-6})$-alkyl, $NH_2$, $NH(C_1-C_6)$-alkyl, $N((C_1-C_6)$-alky$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
piperidinyl,
where the piperidinyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$—$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$;

R13 is F, Cl, Br, I, OH, $CF_3$, $NO_2$, CN, $OCF_3$, $OCHF_2$, —$(C_1-C_6)$-alkylene, —O—$(C_1-C_6)$-alkylene;
phenyl,
where the phenyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
piperidinyl,
where the piperidinyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkylene-(R9), $(C_1-C_6)$-alkylene-(R9), $NH_2$, $NH(C_1-C_6)$-alkylene-(R9), $N((C_1-C_6)$-alkyl$)_2$, $SO_2$-$(C_1-C_6)$-alkylene-(R9), $SO_2$—$C_2H_2F_3$, $SO_2$—$CH_3$, $SO_2$—$NH_2$, $SO_2$—$NH(C_1-C_6)$-alkylene-(R9), $SO_2$—$N((C_1-C_6)$-alkyl$)_2$, COOH, COO—$(C_1-C_6)$-alkylene-(R9), $CONH_2$, $CONH(C_1-C_6)$-alkylene-(R9), $CON((C_1-C_6)$-alkyl$)_2$, $SF_5$;
R7, R8 is H, $(C_1-C_3)$-alkyl;
R9 is H, OH, $OCH_3$, $OCF_3$, $CHF_2$, $CF_3$;
R10 is H, $CONH_2$;
and pharmaceutically compatible salts thereof.

5. The compound of claim 1, wherein the R1 radical therein is bonded as shown in formula Ia and Ib

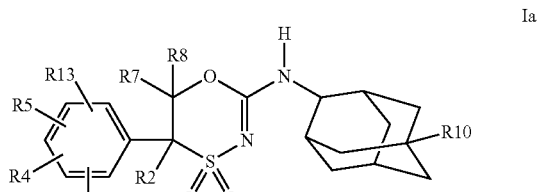

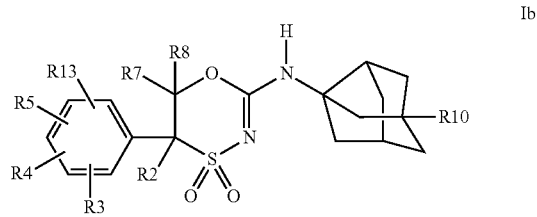

and pharmaceutically compatible salts thereof.

6. A pharmaceutical compound comprising the compound of claim 1, or pharmaceutically acceptable salts thereof, and a pharmaceutically acceptable carrier and/or excipient.

7. The pharmaceutical composition of claim 6, further comprising at least one further active ingredient.

8. The pharmaceutical composition of claim 7, wherein said active ingredient is one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine: fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TR βagonists or amphetamines.

9. A process for preparing pharmaceutical composition comprising mixing the compound of claim 1 with a pharmaceutically suitable carrier and converting said mixture to a form suitable for administration.

10. A method of treating hyperglycemia comprising administering to a patient in need thereof a therapeutically effective amount of the pharmaceutical composition of claim 6.

11. A method of treating diabetes comprising administering to a patient in need thereof a therapeutically effective amount of the pharmaceutical composition of claim 6.

12. A method of treating insulin resistance comprising administering to a patient in need thereof a therapeutically effective amount of the pharmaceutical composition of claim 6.

13. A kit consisting of separate packages of
  a) an effective amount of the compound of claim 1 and
  b) an effective amount of a further active medicament ingredient.

* * * * *